(12) United States Patent
Buchanan et al.

(10) Patent No.: US 8,003,839 B2
(45) Date of Patent: *Aug. 23, 2011

(54) PROCESS FOR GENERATING LINEAR APHA OLEFIN COMONOMERS

(75) Inventors: John Scott Buchanan, Lambertville, NJ (US); Krishnan Sankaranarayanan, South Riding, NJ (US); Milind B. Ajinkya, Oakton, VA (US); Stephen M. Wood, Sterling, VA (US); Anastasios I. Skoulidas, Bristow, VA (US); James R. Lattner, Laporte, TX (US); John F. Walzer, Seabrook, TX (US)

(73) Assignee: Exxonmobil Chemical Patents Inc., Houston, TX (US)

( * ) Notice: Subject to any disclaimer, the term of this patent is extended or adjusted under 35 U.S.C. 154(b) by 1333 days.

This patent is subject to a terminal disclaimer.

(21) Appl. No.: 11/517,871

(22) Filed: Sep. 8, 2006

(65) Prior Publication Data

US 2007/0185360 A1   Aug. 9, 2007

Related U.S. Application Data

(63) Continuation-in-part of application No. 11/346,652, filed on Feb. 3, 2006.

(51) Int. Cl.
*C07C 2/22* (2006.01)
(52) U.S. Cl. ........ 585/513; 585/310; 585/324; 585/329; 585/500; 585/502; 585/510; 585/511; 585/512; 585/520; 585/521; 585/522; 585/523
(58) Field of Classification Search .................. 422/134; 585/513, 511, 512, 310, 324, 329, 500, 502, 585/510, 521, 522, 523
See application file for complete search history.

(56) References Cited

U.S. PATENT DOCUMENTS 3,300,458 A   1/1967   Manyik et al.
3,333,016 A   7/1967   Schultz (Continued)

FOREIGN PATENT DOCUMENTS

CA   2087578   7/1994

(Continued)

OTHER PUBLICATIONS

J. T. Dixon, et. al., "Advances in Selective Ethylene Trimerization—A Critical Overview" in J. Organomet. Chem., 689 (2004) 3641-3668.*

(Continued)

*Primary Examiner* — In Suk Bullock
*Assistant Examiner* — Bradley Etherton

(57) ABSTRACT

The present invention relates to an in-line method for generating comonomer, from monomer, such as ethylene. The comonomer generated is stored prior to transporting to a polyethylene polymerization reactor. The in-line method includes the steps of providing an in-line comonomer synthesis reactor and a downstream gas/liquid phase separator prior to the polymerization reactor; feeding ethylene monomer and a catalyst in a solvent and/or diluent to the comonomer synthesis reactor; reacting the ethylene monomer and the catalyst in solvent and/or diluent under reaction conditions to produce an effluent stream including ethylene monomer and comonomer; passing the effluent stream from the comonomer synthesis reactor to the downstream gas/liquid phase separator to separate a gas stream from a bottom stream, wherein the gas stream is a mixture of ethylene monomer and comonomer; and passing the gas stream to the polymerization reactor to provide the necessary comonomer input.

43 Claims, 12 Drawing Sheets

Process Schematic for the Production of 1-Hexene with 1-Hexene as a Solvent

U.S. PATENT DOCUMENTS

| | | | |
|---|---|---|---|
| 4,472,525 A | 9/1984 | Singleton | |
| 4,511,746 A | 4/1985 | Miller | |
| 4,668,838 A | 5/1987 | Briggs | |
| 4,689,437 A | 8/1987 | Murray | |
| 4,777,315 A | 10/1988 | Levine et al. | |
| 4,853,356 A | 8/1989 | Briggs | |
| 5,000,840 A | 3/1991 | Anthes et al. | |
| 5,137,994 A | 8/1992 | Goode et al. | |
| 5,198,563 A | 3/1993 | Reagen et al. | |
| 5,376,612 A | 12/1994 | Reagen et al. | |
| 5,382,738 A | 1/1995 | Reagen et al. | |
| 5,438,027 A | 8/1995 | Reagen et al. | |
| 5,439,862 A | 8/1995 | Kemp | |
| 5,451,645 A | 9/1995 | Reagen et al. | |
| 5,491,272 A | 2/1996 | Tanaka et al. | |
| 5,523,507 A | 6/1996 | Reagen et al. | |
| 5,541,270 A | 7/1996 | Chinh et al. | |
| 5,543,375 A | 8/1996 | Lashier et al. | |
| 5,550,305 A | 8/1996 | Wu | |
| 5,557,026 A | 9/1996 | Tanaka et al. | |
| 5,563,312 A | 10/1996 | Knudsen et al. | |
| 5,637,660 A | 6/1997 | Nagy et al. | |
| 5,668,249 A | 9/1997 | Baardman et al. | |
| 5,731,487 A | 3/1998 | Tamura et al. | |
| 5,744,677 A | 4/1998 | Wu | |
| 5,750,816 A * | 5/1998 | Araki et al. | 585/512 |
| 5,750,817 A | 5/1998 | Tanaka et al. | |
| 5,763,723 A | 6/1998 | Reagen et al. | |
| 5,811,618 A | 9/1998 | Wu | |
| 5,814,575 A | 9/1998 | Reagen et al. | |
| 5,853,551 A | 12/1998 | Boucot et al. | |
| 5,856,257 A | 1/1999 | Freeman et al. | |
| 5,856,610 A | 1/1999 | Tamura et al. | |
| 5,856,612 A * | 1/1999 | Araki et al. | 585/522 |
| 5,859,303 A | 1/1999 | Lashier | |
| 5,910,619 A | 6/1999 | Urata et al. | |
| 5,919,996 A | 7/1999 | Freeman et al. | |
| 5,968,866 A | 10/1999 | Wu | |
| 6,004,256 A * | 12/1999 | Townsend et al. | 585/517 |
| 6,031,145 A | 2/2000 | Commereuc et al. | |
| 6,103,657 A | 8/2000 | Murray | |
| 6,133,495 A | 10/2000 | Urata et al. | |
| 6,136,748 A | 10/2000 | Smith | |
| 6,137,748 A | 10/2000 | Murakami | |
| 6,265,513 B1 | 7/2001 | Murray et al. | |
| 6,268,447 B1 | 7/2001 | Murray et al. | |
| 6,274,783 B1 | 8/2001 | Gildert et al. | |
| 6,277,841 B1 | 8/2001 | Rajagopalan et al. | |
| 6,303,719 B1 | 10/2001 | Murray et al. | |
| 6,320,002 B1 | 11/2001 | Murray et al. | |
| 6,320,005 B1 | 11/2001 | Murray | |
| 6,337,297 B1 * | 1/2002 | Mimura et al. | 502/117 |
| 6,344,594 B1 | 2/2002 | Sen et al. | |
| 6,380,451 B1 | 4/2002 | Kreischer et al. | |
| 6,399,843 B1 | 6/2002 | Koves | |
| 6,423,791 B1 | 7/2002 | Kral | |
| 6,437,161 B1 | 8/2002 | Mihan et al. | |
| 6,455,648 B1 | 9/2002 | Freeman et al. | |
| 6,489,263 B2 | 12/2002 | Murray et al. | |
| 6,521,806 B1 | 2/2003 | Tamura et al. | |
| 6,559,091 B1 | 5/2003 | Moody et al. | |
| 6,583,083 B2 | 6/2003 | Murray et al. | |
| 6,610,627 B2 | 8/2003 | Murray | |
| 6,610,805 B1 | 8/2003 | Guram et al. | |
| 6,706,829 B2 | 3/2004 | Boussie et al. | |
| 6,713,577 B2 * | 3/2004 | Boussie et al. | 526/161 |
| 6,727,361 B2 | 4/2004 | LaPointe et al. | |
| 6,750,345 B2 | 6/2004 | Boussie et al. | |
| 6,800,702 B2 * | 10/2004 | Wass | 526/124.3 |
| 6,828,269 B2 | 12/2004 | Commereuc et al. | |
| 6,828,397 B2 | 12/2004 | Boussie et al. | |
| 6,844,290 B1 | 1/2005 | Maas et al. | |
| 6,844,920 B2 | 1/2005 | Louellau | |
| 6,900,152 B2 | 5/2005 | Yoshida et al. | |
| 7,157,612 B2 | 1/2007 | Ewert et al. | |
| 7,214,842 B2 | 5/2007 | Mihan et al. | |
| 7,858,833 B2 * | 12/2010 | Buchanan et al. | 585/513 |
| 2001/0034297 A1 | 10/2001 | Murray et al. | |
| 2002/0035029 A1 | 3/2002 | Yoshida et al. | |
| 2002/0065379 A1 | 5/2002 | Murray | |
| 2002/0137845 A1 | 9/2002 | Boussie et al. | |
| 2002/0142912 A1 | 10/2002 | Boussie et al. | |
| 2002/0147288 A1 | 10/2002 | Boussie et al. | |
| 2002/0153697 A1 | 10/2002 | Amirola | |
| 2002/0156279 A1 | 10/2002 | Boussie et al. | |
| 2002/0173419 A1 | 11/2002 | Boussie et al. | |
| 2002/0177711 A1 | 11/2002 | LaPointe et al. | |
| 2002/0183574 A1 | 12/2002 | Dixon et al. | |
| 2003/0130551 A1 | 7/2003 | Drochon et al. | |
| 2003/0149198 A1 | 8/2003 | Small et al. | |
| 2003/0153697 A1 | 8/2003 | Boussie et al. | |
| 2003/0166456 A1 | 9/2003 | Wass | |
| 2004/0122247 A1 | 6/2004 | Boussie et al. | |
| 2004/0122271 A1 | 6/2004 | Van Zon et al. | |
| 2004/0228775 A1 * | 11/2004 | Ewert et al. | 422/131 |
| 2004/0236163 A1 | 11/2004 | Ewert et al. | |
| 2005/0020788 A1 | 1/2005 | Wass | |
| 2005/0020866 A1 | 1/2005 | Kobayashi et al. | |
| 2005/0113524 A1 | 5/2005 | Stevens et al. | |
| 2005/0197521 A1 | 9/2005 | Kreischer | |
| 2006/0094839 A1 | 5/2006 | Diamond et al. | |
| 2006/0094867 A1 | 5/2006 | Diamond et al. | |
| 2006/0173226 A1 | 8/2006 | Blann et al. | |
| 2006/0211903 A1 | 9/2006 | Blann et al. | |
| 2006/0229480 A1 | 10/2006 | Blann et al. | |
| 2006/0247339 A1 | 11/2006 | Harashina et al. | |
| 2006/0247399 A1 | 11/2006 | McConville et al. | |
| 2006/0247483 A1 | 11/2006 | McConville et al. | |
| 2006/0293546 A1 | 12/2006 | Nabika | |
| 2007/0027350 A1 | 2/2007 | Nabika | |
| 2007/0049781 A1 | 3/2007 | Brown et al. | |
| 2007/0185358 A1 | 8/2007 | Buchanan et al. | |
| 2007/0185364 A1 | 8/2007 | Buchanan et al. | |

FOREIGN PATENT DOCUMENTS

| | | |
|---|---|---|
| CA | 2115639 | 9/1994 |
| CN | 1256968 | 6/2000 |
| EP | 237 079 | 7/1990 |
| EP | 416 304 | 3/1991 |
| EP | 537 609 | 4/1993 |
| EP | 608 447 | 8/1994 |
| EP | 614 865 | 9/1994 |
| EP | 622 347 | 11/1994 |
| EP | 668 106 | 8/1995 |
| EP | 699 648 | 3/1996 |
| EP | 706 983 | 4/1996 |
| EP | 780 353 | 6/1997 |
| EP | 889 061 | 1/1999 |
| EP | 993 464 | 4/2000 |
| EP | 1 110 930 | 6/2001 |
| EP | 1 308 450 | 5/2003 |
| EP | 1 364 974 | 11/2003 |
| EP | 1 607 415 | 12/2005 |
| GB | 2 298 864 | 9/1996 |
| JP | 07010780 | 1/1995 |
| JP | 06515873 | 3/1995 |
| JP | 07215896 | 8/1995 |
| JP | 07267881 | 10/1995 |
| JP | 09020692 | 1/1997 |
| JP | 09020693 | 1/1997 |
| JP | 09268133 | 10/1997 |
| JP | 09268134 | 10/1997 |
| JP | 09268135 | 10/1997 |
| JP | 10-007712 | 1/1998 |
| JP | 10007593 | 1/1998 |
| JP | 10007594 | 1/1998 |
| JP | 10007595 | 1/1998 |
| JP | 10036431 | 2/1998 |
| JP | 10036432 | 2/1998 |
| JP | 10045638 | 2/1998 |
| JP | 10087518 | 4/1998 |
| JP | 11092407 | 4/1999 |
| JP | 11092408 | 4/1999 |
| JP | 11222445 | 8/1999 |
| JP | 10007712 | 1/2000 |
| JP | 2000176291 | 6/2000 |
| JP | 2000202299 | 7/2000 |

| | | |
|---|---|---|
| JP | 2000212212 | 8/2000 |
| JP | 2007-010780 | 1/2001 |
| JP | 2001009290 | 1/2001 |
| JP | 2001187345 | 7/2001 |
| JP | 2002045703 | 2/2002 |
| JP | 2002066329 | 3/2002 |
| JP | 2002102710 | 4/2002 |
| JP | 2002172327 | 6/2002 |
| JP | 2002200429 | 7/2002 |
| JP | 2002205960 | 7/2002 |
| JP | 2002233765 | 8/2002 |
| JP | 3351068 | 11/2002 |
| JP | 2003071294 | 3/2003 |
| JP | 3540827 | 7/2004 |
| JP | 3540828 | 7/2004 |
| JP | 3577786 | 10/2004 |
| WO | WO 97/37765 | 10/1997 |
| WO | WO 99/01460 | 1/1999 |
| WO | WO 99/19280 | 4/1999 |
| WO | WO 00/37175 | 6/2000 |
| WO | WO 00/50470 | 8/2000 |
| WO | WO 01/10876 | 2/2001 |
| WO | WO 01/47839 | 7/2001 |
| WO | WO 01/48028 | 7/2001 |
| WO | WO 01/68572 | 9/2001 |
| WO | WO 01/83447 | 11/2001 |
| WO | WO 02/04119 | 1/2002 |
| WO | WO 02/38628 | 5/2002 |
| WO | WO 02/46249 | 6/2002 |
| WO | WO 02/066404 | 8/2002 |
| WO | WO 02/066405 | 8/2002 |
| WO | WO 02/083306 | 10/2002 |
| WO | WO 03/004158 | 1/2003 |
| WO | WO 03/053890 | 7/2003 |
| WO | WO 03/053891 | 7/2003 |
| WO | WO 2004/056477 | 7/2004 |
| WO | WO 2004/056478 | 7/2004 |
| WO | WO 2004/056479 | 7/2004 |
| WO | WO 2004/056480 | 7/2004 |
| WO | 2004/064798 | 8/2004 |
| WO | WO 2004/083263 | 9/2004 |
| WO | WO 2005/123633 | 12/2005 |
| WO | WO 2005/123884 | 12/2005 |
| WO | WO 2006/096881 | 9/2006 |
| WO | WO 2007/007272 | 1/2007 |

OTHER PUBLICATIONS

J. Fair, "Distillation" in Kirk-Othmer Encyclopedia of Chemical Technology, John Wiley, 1993, posted on-line Aug. 17, 2001.*

Sundaram, et. al., "Ethylene" in Kirk-Othmer Encyclopedia of Chemcial Technology, John Wiley, 2001, posted on-line Apr. 16, 2001.*

Seador, et al., "Distillation" in Perry's Chemical Engineers Handbook, R. H. Perry, ed., 1997, McGraw-Hill.*

Agrawal, et al.,"More Operable Fully Thermally Coupled Distillation Column Configurations," Trans. IChemE, 77(A), 543-553, (1999).*

Agrawal, et al., "More Operable Fully Thermally Coupled Distillation Column Configurations," Trans. IChemE, 77(A), 543-553, (1999).*

Seador, et al., "Distillation" in Perry's Chemical Engineer's Handbook, John Wiley (1997), posted on-line Mar. 1, 2001.*

Seador, et al., "Distillation" in Perry's Chemical Engineer's Handbook, 7th ed., 1997, McGraw-Hill, posted on-line Mar. 1, 2001.*

A. Ranwell et al., "Potential Application of Ionic Liquids for Olefin Oligomerization,"ACS Symposium Series, Chapter 12, 2002, 818, pp. 147-160.

R.D. Kohn et al., 1,3,5-Triazacyclohexane Complexes of Chromium as Homogeneous Model Systems for the Phillips Catalyst, ACS Symposium Series, 2003, 857, pp. 88-100.

K.R. Dunbar et al., "Structure of [HTMPP]$_3$W$_2$CL$_9$[HTMPP=Tris(2,4,6-trimethoxyphenyl)-phosphonium]," Acta Cryst., 1991, C47, pp. 23-26.

D.H. Morgan et al., "The Effect of Aromatic Ethers on the Trimerisation of Ethylene using a Chromium Catalyst and Aryloxy Ligands," Adv. Synth. & Catalysis, 2003, 345, pp. 939-942.

Y.Yang et al., "Roles of chloro compound in homogeneous [Cr(2-ethylhexanoate)$_3$/2,5-dimethylpyrrole/triethylaluminum/chloro compound] catalyst system for ethylene trimerization," Applied Catalysis A: General, 2000, 193, pp. 29-38.

H. Mahomed et al., "Ethylene trimerisation catalyst based on substituted cyclopentadienes," Applied Catalysis A: General, 2003, 255, pp. 355-359.

Kohn et al., Triazacyclohexane complexes of chromium as highly active homogeneous model sytstems for the Philips catalyst, Chem. Commun., 2000, pp. 1927-1928.

A. Carter et al., "High activity ethylene trimerisation catalysts based on diphosphine ligands," Chem. Commun., 2002, pp. 858-859.

D.S. McGuinness et al., "Novel Cr-PNP complexes as catalysts for the trimerisation of ethylene," Chem. Commun. 2003, pp. 334-335.

C.N. Nenu et al., "Single-site heterogeneous Cr-based catalyst for the selective trimerisation of ethylene," Chem. Commun., 2005, pp. 1865-1867.

K. Blann et al., "Highly selective chromium-based ethylene trimerisation catalysts with bulky diphosphinoamine ligands," Chem. Commun., 2005, pp. 620-621.

M.J. Overett et al., "Ethylene trimerisation and tetramerisation catalysts with polar-substituted diphosphinoamine ligands," Chem. Commun., 2005, pp. 622-624.

Hecheng Shuzhi Ji Suliao, China Synthetic Resin and Plastics, 2001, 18(2), 23-25, 43.

T. Imamoto et al., "Synthesis and reactions of Optically Pure Cyclohexyl (o-methoxyphenyl)phosphine-Borane and t-Butyl-(o-methoxyphenyl)phosphine-Borane," Heteroatom Chemistry, 1993, vol. 4, No. 5, pp. 475-486.

N. J. Robertson et al., "Chromium(II) and Chromium (III) Complexes Supported by Tris(2-pyridylmethyl)amine: Synthesis, Structures, and Reactivity," Inorg. Chem., 42, pp. 6876-6885 (2003).

L. Hirsivaara et al., "M(CO)$_6$ (M=CR, Mo, W) derivatives of (o-anisyl)diphenylphosphine, bis(o-anisyl)phenylphosphine tris(o-anisyl)phosphine and (p-anisyl)bis(o-anisyl)phosphine," Inorganica Chimica ACTA, 2000, 307, pp. 47-56.

D.S. McGuinness et al., "First Cr(III)-SNS Complexes and Their Use as Highly Efficient Catalysts for the Trimerization of Ethylene to 1-Hexene," J. Am. Chem. Soc., 2003, 125, pp. 5272-5273.

C. Andes et al., "New Tantalum-based Catalyst System for the Selective Trimerization of Ethene to 1-Hexene," J. Am. Chem. Soc., 2001, 123, pp. 7423-7424.

T.Agapie et al., "Mechanistic Studies of the Ethylene Trimerization Reaction with Chromium-Diphosphine Catalysts: Experimental Evidence for a Mechanism Involving Metallacyclic Intermediates," J. Am. Chem. Soc., 126, 2004, pp. 1304-1305.

A. Bollmann et al., "Ethylene Tetramerization: A New Route to Produce 1-Octene in Exceptionally High Selectivities," J. Am. Chem. Soc., 126, 2004, pp. 14712-14713.

A. Ariffin et al., "The asymmetric synthesis of phosphorus- and sulfur-containing tricarbonyl(n$^6$-arene) chromium complexes using the chiral base approach," J. Chem. Soc., Perkin Trans., 1, 1999, pp. 3177-3189.

T. Monoi et al., "Silica-supported Cr[N(SiMe$_3$)$_2$]$_3$/isobutylalumoxane catalyst for selective ethylene trimerization," Journal of Mol. Catalysis A: Chemical, 187, 2002, pp. 135-141.

J.T. Dixon et al., "Advances in selective ethylene trimerisation—a critical overview," Jrnl. of Organometallic Chem., 689, 2004, pp. 3641-3668.

R.M. Manyik et al., "A Soluble Chromium-Based Catalyst for Ethylene Trimerization and Polymerization," Journal of Catalysts, 1977, 47, pp. 197-209.

L. Hirsivaara et al., "Organometallic derivatives of multidentate phosphines [o-(methylthio)phenyl]diphenylphosphine and bis(o-(methylthio)phenyl(phenylphosphine: preparation and characterization of group 6 metal carbonyl derivatives," Jrnl. of Organometallic Chem., 579, 1999, pp. 45-52.

J. Pietsch et al., "Koordinationschemie funktioneller Phosphine II. Carbonyl(nitrosyl) wolfram-Komplexe mit 2-Diphenyl-phosphphinoanisol sowie 2-Diphenylphosphinoanilid, -benzoat und -phenolat als Liganden," Journal of Organometallic Chemistry, 495, 1995, pp. 113-125.

L. Dahlenburg et al., "Koordinationschemie funktioneller Phosphane VIII. Tetracarbonylkomplexe des Wolframs und Molybdans mit 2-(Diphenylphosphanyl)anilin-Liganden," Journal of Organometallic Chemistry, 585, 1999, pp. 225-233.

D. de Wet-Roos et al., "Homogeneous Tandem Catalysis of Bis(2-decylthioethyl)amine-Chromium Trimerization Catalyst in Combination with Metallocene Catalysts," Macromolecules, 2004, 37, pp. 9314-9320.

R. Blom et al., "1,3,5-Triazacyclohexane Complexes of Chromium as Homogeneous Model Systems for the Phillips Catalyst," Organometallic Catalysts and Olefin Polymerization, 2001, pp. 147-155.

K. Burgess, Stereochemically Matched (and Mismatched) Bisphosphine Ligands: DIOP-DIPAMP Hybrids, Organometallics, 1992, 11, pp. 3588-3600.

K.R. Dunbar et al., Carbon Monoxide Reactions of the Fluxional Phosphine Complex $(n^3\text{-PR}_3)\text{Mo(Co)}_3$ (R=2,4,6-Trimethoxyphenyl), Organometallics, 1994, 13, pp. 2713-2720.

G. Boni et al., "Heterobimetallic Dibridged Complexes [$Cp_2Ta$(u-CO)(u-$PMe_2$)M'($CO)_4$] (M'=Cr, W): Synthesis and Reactivity toward Two-Electron Donor Ligands L (L=$PR_3$, $Me_2P(CH_2)nPMe_2$, CNR)," Organometallics, 1995, 14, pp. 5652-5656.

T. Agapie et al.; "A Chromium-Diphosphine System for Catalytic Ethylene Trimerization: Synthetic and Structural Studies of Chromium Complexes with a Nitrogen-Bridged Diphosphine Ligand with *ortho*-Methoxyaryl Substituents"; Organometallics, 25; 2006, pp. 2733-2742.

R.L. Wife et al., "Phosphine Oxide Anions in the Synthesis of Phosphine Ligands," Synthesis, 1983, pp. 71-73.

P.J.W. Deckers et al., "Catalytic Trimerization of Ethene with Highly Active Cyclopentadienyl-Arene Titanium Catalysts," Organometallics, 2002, 21, pp. 5122-5135.

S. Naqvi, "1-Hexene From Ethylene by the Phillips Trimerization Technology," available on-line at http://www.sriconsulting.com/PEP/Reports/Phase_95/RW95-1-1/RW95-1-8.html, Dec. 1997.

R. Agrawal "*More Operable Fully Thermally Coupled Distillation Column Configurations for Multicomponent Distillation*", Transactions of the Institution of Chemical Engineers, 1999, 77(A), pp. 543-553.

Y.T. Shah, et al. "*Design Parameters Estimations for Bubble Column Reactors*", American Institute of Chemical Engineers' Journal, 1982, vol. 28 No. 3, pp. 353-379.

K.M. Sundaram, et al. "*Ethylene*" Kirk-Othmer Encyclopedia of Chemical Technology, John Wiley, 2001, vol. 10, pp. 593-632, posted on-line Apr. 16, 2001.

Gokel, G.W., ed. Dean's Handbook of Organic Chemistry, Mc-Graw-Hill, 2004, 2nd edition, avaliable on-line at www.knovel.com.

Small, B.L. et al., "New Chromium Complexes for Ethylene Oligomerization: Extended Use of Tridentate Ligands in Metal-Catalyzed Olefin Polymerization," Macromolecules, vol. 37, No. 12, 2004, pp. 4375-4386.

Walas, S., "*Chemical Reactors*" Perry's Chemical Engineers' Handbook 7th Edition, 1997, pp. 26-36-23-40.

* cited by examiner

Process Schematic for the Production of 1-Hexene with 1-Hexene as a Solvent

Process Schematic for the Production of 1-Hexene with Toluene as a Solvent

Process Schematic for the Production of 1-Hexene with Isopentane as a Solvent at 800 psia Process Schematic for the Production of 1-Butene with Isopentane as a Solvent
at 800 psia Process Schematic for the Production of 1-Hexene with Isopentane as a Solvent and Polymer Grade Feed

A42
 A43
 A44
 A45
 A46
 A47
 A48
 A49
 A50
 A51
 A52
 A72
 A73

A63

A64

A65

A66

A67

A68

A69

A70

A71

A74

A75 ized alpha olefins from monomer from specific catalysts and or
PROCESS FOR GENERATING LINEAR APHA OLEFIN COMONOMERS

PRIORITY CLAIM

This invention is a continuation in part of U.S. Ser. No. 11/346,652, filed Feb. 3, 2006 and assigned to ExxonMobil Research and Engineering.

FIELD OF THE INVENTION

The present invention relates to the field of chemical reaction and separation processes. It more particularly relates to an improved process for generating linear alpha olefin comonomers from monomer from specific catalysts and or catalyst systems.

BACKGROUND

Olefin polymerization, especially ethylene polymerization, can benefit from the addition of longer-chain comonomers, such as 1-butene, 1-hexene, and 1-octene, to produce linear low density polyethylene (LLDPE). LLDPE produced from 1-butene, 1-hexene and 1-octene accounts for a large percentage of the polyethylene resin market. In general, polyethylene plants buy butene, hexene and octene, which are produced in separate plants that typically produce a range of even-numbered alpha olefins from ethylene. It can be expensive to purchase these materials, and they add to the complexity of transport, storage and handling. An attractive alternative is to make the comonomer directly from the ethylene at the site where they will be used, if this can be done cleanly and economically.

The review article "Advances in selective ethylene trimerisation—a critical review" by Dixon et al. (J. Organometallic Chemistry 689 (2004) 3641-3668), herein incorporated by reference in its entirety, describes many different catalysts for trimerization. These catalyst systems contain chromium, and with particular ligands, such as aromatic species (e.g. pyrrolyl) or multidentate heteratomic species. The chromium catalysts are typically activated by alkylaluminum and/or alkyaluminoxane activators. The article also describes group 4 and 5 early transition metals, such as Zr, V, Ta and Ti, and group 8 late transition metals, such as Ni, for showing some activity in trimerization.

Phillips has developed chromium-based catalysts that are selective towards making 1-hexene from ethylene. The major byproduct appears to be 1-decene. SRI Consulting PEP Review 95-1-8 entitled "1-Hexene From Ethylene By the Phillips Trimerization Technology," available on-line at http://www.sriconsulting.com/PEP/Reports/Phase_95/RW95-1-8/RW95-1-8.html, herein incorporated by reference in its entirety, describes the Phillips standalone process for making 1-hexene based on Phillips trimerization technology. In this process, ethylene and a homogeneous catalyst in a solvent are fed to a reactor. The reactor is a stirred tank with heat removal coils. This reactor operates at 115 deg. C. and 49 kg/cm2 (~700 psia), and converts about 75% of the ethylene fed. This reactor is 42,300 gal (5655 ft3). A spare reactor is provided, since waxy buildup on the cooling coils may necessitate lengthy shutdowns for cleaning. The feed is approximately 29,000 lb/hr cyclohexane solvent (with catalyst) plus 36,000 lb/hr ethylene (27,000 fresh feed and 9,000 recycle). It is estimated that the resident time in the reactor is on average 4 to 5 hours. Selectivity in the SRI process by weight is about 93% to 1-hexene, 1% to other C6s, 1% to octenes, and 5% to decenes. The effluent from the reactor is contacted with octanol to kill the catalyst from further reaction. The effluent then goes to an ethylene column where unconverted ethylene is taken overhead and recycled to the reactor. Because ethylene is so volatile, an expensive cryogenic column must be used. Four more distillation columns follow to remove hexene, cyclohexane solvent, octene, and decene. Some of these are run under vacuum, which again makes for expensive hardware and operations. The bottoms from the decene tower is a small stream containing mainly octanol and deactivated catalyst. This stream is treated with caustic and then with acid to remove the catalyst by precipitation and by solution in an aqueous phase, which is separated from the organic phase containing the octanol. Octanol may then be recycled.

U.S. Pat. No. 5,382,738 to Reagen et al., herein incorporated by reference in its entirety, discloses catalyst systems comprising inorganic oxides, modified with a metal alkyl and an unsaturated hydrocarbon, which can be used to support a metal source, such as, for example, chromium, and a pyrrole-containing compound. The resultant catalyst systems can be used to oligomerize and/or trimerize olefins via a slurry process.

U.S. Pat. No. 5,451,645 to Reagen et al., herein incorporated by reference in its entirety, discloses novel chromium-containing compounds prepared by forming a mixture of a chromium salt, a metal amide, and an ether. These novel chromium-containing, or chromium pyrrolide compounds, with a metal alkyl and an unsaturated hydrocarbon, can be used as a co-catalyst system in the presence of an olefin polymerization catalyst system to produce a comonomer in-situ with trimerization.

U.S. Pat. No. 5,543,375 to Lashier et al., herein incorporated by reference in its entirety, discloses a process to stabilize and/or reactivate an olefin production catalyst system, which comprises contacting an olefin production catalyst system, either before or after use, with an aromatic compound.

European Patent No. 0 668 106 to Freeman et al., herein incorporated by reference in its entirety, discloses a process which will effectively deactivate, inhibit, and/or "kill" an olefin production catalyst, and halt polymer production in an olefin production process. It further provides for a process which can remove an olefin production catalyst from the product stream, and recover catalyst by-products for recycle, and/or recovery.

A need exists for an improved process to generate linear alpha olefin comonomers from monomer. More particularly, a need exists for a reaction and separation process to generate 1-butene, 1-hexene, or 1-octene from ethylene monomer for subsequent isolation or storage prior to being used in a polymerization reactor or other chemical process requiring such comonomer.

With regard to specific oligomerization catalyst systems, particularly ethylene trimerization systems, the following references are of interest: U.S. Pat. No. 4,668,838; U.S. Pat. No. 5,137,994; U.S. Pat. No. 5,198,563; U.S. Pat. No. 5,382,738; U.S. Pat. No. 5,438,027; U.S. Pat. No. 5,523,507; U.S. Pat. No. 5,543,375; U.S. Pat. No. 5,856,257; EP 0 416 304 B1; EP 0 608 447 B1; EP 0 780 353 B1; CA 2,087,578; U.S. Pat. No. 5,491,272; U.S. Pat. No. 5,750,817; U.S. Pat. No. 6,133,495; U.S. Pat. No. 5,750,816; U.S. Pat. No. 5,856,612; U.S. Pat. No. 5,910,619; EP 0 537 609; CA 2,115,639; EP 0 614 865 B1; EP 0 699 648 B1; WO03/053890; McGuinness et al., *J. Am. Chem. Soc.* 125, 5272-5273, (2003); WO02/083306A2; WO03/004158A2; U.S. Pat. No. 5,968,866; WO02/04119A1 (and related U.S. Pat. No. 6,800,702, U.S. 2003/166456, and U.S. 2005/020788); *J. Am. Chem. Soc.* 123, 7423-7424 (2001); WO01/68572A1; WO02/066404A1; WO04/056477; WO04/056478; WO04/056479; WO04/056480; EP 1 110

930 A1; U.S. Pat. No. 3,333,016; U.S. Pat. No. 5,439,862; U.S. Pat. No. 5,744,677; U.S. Pat. No. 6,344,594; and U.S. Pat. App. Pub. No. 2002/0035029A1; Carter et al., *Chem. Commun.*, 2002, pp. 858-859; JP 2001187345A2; JP 2001187345A2.

Likewise additional references regarding ethylene trimerization catalysts include: WO01/10876, WO97/37765, EP 1 110 930 A1, U.S. Pat. No. 3,333,016, U.S. Pat. No. 5,439,862, U.S. Pat. No. 5,744,677, U.S. Pat. No. 6,344,594, U.S. Pat. No. 4,689,437, U.S. Pat. No. 4,472,525, U.S. Pat. No. 5,668,249, U.S. Pat. No. 5,856,610, U.S. Pat. No. 3,300,458, U.S. Pat. App. Pub. No. 2002/0035029A1, *Journal of Organometallic Chemistry* 579 (1999) 45-52, *Organometallics* 1992, 11 3588-3600, *Organometallics* 1995, 14, 5652-5656, *J. Chem. Soc., Perkin Trans.* 1, 1999, 3177-3189, *Organometallics* 1994, 13, 2713-2720, *Journal of Organometallic Chemistry*, Volume 585, Issue 2, 15 Aug. 1999, pgs 225-233, *Acta Cryst.* (1991). C47, 23-26, *Journal of Organometallic Chemistry*, Vol 495, No. 1, 14 Jun. 1995, pgs 113-125, *Inorg. Chim. ACTA* (2000), 307(1-2), 47-56. *Chem. Commun.* 2005, 620-621, *Chem. Commun.* 2005, 622-624, *Chem. Commun.* 2005, 1865-1867, *J. Am. Chem. Soc.* 2004, 126, 14712-14713, *J. Am. Chem. Soc.* 2004, 126, 1304-1305, *Macromolecules*, 2004, 37, 9314-9320, *Journal of Organometallic Chemistry*, 2004, 689, 3641-3668, *Heteroatom Chemistry*, 1993, 4, 475-486; *Synthesis*, 1983, 1, 71-73; U.S. Pat. No. 6,800,702; *Chem. Commun.*, 2002, 8, 858-859; *PERP Report*, Nexant/Chem Systems, 2004, 57-60; *Dangdai Shiyou Shihu*, 2002, 10, 25-29; *ACS Symposium Series*, 2002, 818, 147-160; *Journal of Organometallic Chemistry*, 2004 689, 3641-3668; U.S. Pat. No. 4,668,838; U.S. Pat. No. 4,777,315; U.S. Pat. No. 4,853,356; U.S. Pat. No. 5,744,677; EP-608447; U.S. Pat. No. 5,557,026; JP06515873; U.S. Pat. No. 5,750,817; U.S. Pat. No. 5,731,487; EP-622347; U.S. Pat. No. 5,376,612; U.S. Pat. No. 5,382,738; JP3540827 B2; JP3540828 B2; JP3351068 B2; U.S. Pat. No. 5,563,312; JP07215896; JP07267881; U.S. Pat. No. 6,521,806; EP-706983; U.S. Pat. No. 5,523,507; U.S. Pat. No. 5,910,619; U.S. Pat. No. 5,550,305; U.S. Pat. No. 5,750,816; GB2298864; JP3577786 B2; JP09020692; JP09020693; U.S. Pat. No. 5,859,303; U.S. Pat. No. 5,856,612; U.S. Pat. No. 6,133,495; JP09268133; JP09268134; JP09268135; JP10007593; JP10007594; JP10007595; JP10036431; JP10036432; JP10045638; JP10087518; U.S. Pat. No. 5,763,723; U.S. Pat. No. 5,811,618; U.S. Pat. No. 5,814,575; U.S. Pat. No. 6,031,145; U.S. Pat. No. 5,856,257; JP111092407; JP111092408; U.S. Pat. No. 2,004,228775; U.S. Pat. No. 5,919,996; JP11222445; U.S. Pat. No. 5,968,866; U.S. Pat. No. 6,610,805; CN1256968; JP2000176291; JP2000202299; U.S. Pat. No. 6,337,297; JP2000212212; JP2001009290; U.S. Pat. No. 2,002,183574; U.S. Pat. No. 6,828,269; WO200147839 U.S. Pat. No. 6,455,648; WO200183447; JP2002045703; JP2002066329; JP2002102710; U.S. Pat. No. 2,002,035029; JP2002172327; JP2002200429; JP2002233765; WO200283306; WO2003004158; JP2002205960; U.S. Pat. No. 2,003,130551; WO2003053890; WO2003053891; JP2003071294; U.S. Pat. No. 2,003,149198; U.S. Pat. No. 2,004,122271; WO2004056479; WO2004056478; WO2004083263; *Journal of Catalysis*, 1977, 47, 197-209; *J. Am. Chem. Soc.*, 1989, 11, 674-675; *Applied Catalysis, A* (General) 2000, 193, 29-38; *Hecheng Shuzhi Ji Suliao*, 2001, 18, 23-25, 43; *Organometallic Catalysts and Olefin Polymerization*, 2001, 147-155; *J. Mol. Catalysis A: Chemical* (2002), 187, 135-141; *J. Am. Chem. Soc.*, 2002, 125, 5272-5273; *Chem. Commun.* 2003, 3, 334-335; *Beijing Huagong Daxue Xuebao, Ziran Kexueban*, 2003, 30, 80-82; *Adv. Synth. & Catalysis*, 2003, 345, 939-942; *Applied Catalysis, A: General*, 2003, 255, 355-359; *J. Am. Chem. Soc.* 2004, 126, 1304-1305; *ACS Symposium Series*, 2003, 857 (Beyond Metallocenes), 88-100; and *J. Am. Chem. Soc.*, 2004, 126, 14712-14713. Although the catalyst compositions in each of the above described references may be useful for the trimerization of ethylene, there remains a desire to improve the performance of olefin oligomerization catalysts from the standpoint of productivity and selectivity for oligomers such as 1-hexene or 1-octene, particularly where use in a commercial process, particularly an in-line process, is concerned.

Several pyridyl amine catalyst complexes have been disclosed for the polymerization or copolymerization of ethylene, propylene, isobutylene, octene, and styrene by Symyx Technologies, Inc. in U.S. Pat. Nos. 6,713,577, 6,750,345, 6,706,829, 6,727,361, and 6,828,397. Pyridyl amines were also disclosed in U.S. Pat. Nos. 6,103,657 and 6,320,005, assigned to Union Carbide Chemical and Plastics Technology Corporation, in which zirconium was used as the metal center, and the catalyst complex was used to polymerize alpha-olefins, and in U.S. Pat. No. 5,637,660, assigned to Lyondell Petrochemical Company, which also describes Group 4 complexes of pyridyl amine ligands. Robertson et al., *Inorg. Chem.* 42, pp 6875-6885 (2003), discloses chromium complexes of tris(2-pyridylmethyl)amine for ethylene polymerization.

This invention also relates to U.S. patent application Ser. Nos. 60/611,943, 11/232,982 and 11/233,227.

This invention also relates to U.S. Ser. No. 11/844,562, filed Aug. 24, 2007 assigned to ExxonMobil Chemical Patents Inc.; U.S. Ser. No. 11/371,614, filed Mar. 9, 2006, assigned to ExxonMobil Chemical Patents Inc.; and U.S. Ser. No. 11/371,983, filed Mar. 9, 2006, assigned to ExxonMobil Chemical Patents Inc.

This invention also relates to U.S. Ser. No. 11/346,651, filed Feb. 3, 2006 and U.S. Ser. No. 11/346,652, filed Feb. 3, 2006, both assigned to ExxonMobil Research and Engineering.

SUMMARY OF THE INVENTION

This invention relates to the oligomerization, and more specifically the trimerization and/or tetramerization of C2 to C12 olefins, preferably alpha-olefins, preferably ethylene using the ligand-metal-precursor-combinations, metal-ligand-complexes, and/or catalyst systems described herein in the unique processes for generating comonomer described herein. Specifically, this invention relates to the trimerizing and/or tetramerizing of ethylene to form 1-hexene and/or 1-octene using the ligand-metal-precursor-combinations, metal-ligand-complexes, and/or catalyst systems described herein in the unique processes for generating comonomer described herein.

It has been discovered that it is possible to selectively make 1-butene, 1-hexene and other linear alpha olefin comonomers from ethylene monomer via a simpler and less expensive process.

According to the present disclosure, an advantageous method for preparing linear alpha olefin comonomers from ethylene monomer comprises the following steps: providing one or more comonomer synthesis reactors configured in series, and one or more downstream gas/liquid phase separators configured in series; feeding an ethylene monomer, and a catalyst in a solvent and or diluent to the one or more comonomer synthesis reactors; reacting in the one or more comonomer synthesis reactors the ethylene monomer and the catalyst in solvent and or diluent under reaction conditions to produce an effluent stream comprising unreacted ethylene monomer, the catalyst in a solvent and or diluent, and comonomer; passing the effluent stream to the one or more downstream gas/liquid phase separators to form a gas stream of the unreacted ethylene monomer, and a liquid stream of the comonomer and the catalyst in a solvent and or diluent; recycling to the one or more comonomer synthesis reactors the unreacted ethylene monomer and a portion of the liquid stream; and storing a remaining portion of the liquid stream for subsequent processing of the comonomer; wherein the comonomer is selected from the group consisting of 1-butene, 1-hexene, 1-octene, 1-decene and mixtures thereof, and is similar in composition to the solvent and or diluent.

A further aspect of the present disclosure relates to an advantageous method for preparing linear alpha olefin comonomers from ethylene monomer, which comprises the following steps: providing one or more comonomer synthesis reactors configured in series, one or more downstream gas/liquid phase separators configured in series, and one or more distillation columns configured in series; feeding an ethylene monomer, and a catalyst in a solvent and or diluent to the one or more comonomer synthesis reactors; reacting in the one or more comonomer synthesis reactors the ethylene monomer and the catalyst in solvent and or diluent under reaction conditions to produce an effluent stream comprising unreacted ethylene monomer, the catalyst in a solvent and or diluent, and comonomer; passing the effluent stream to the one or more downstream gas/liquid phase separators to form a gas stream of the unreacted ethylene monomer, and a liquid stream of the comonomer and the catalyst in a solvent and or diluent; passing the liquid stream of the comonomer and the catalyst in a solvent and or diluent to the one or more distillation columns to separate the comonomer from the catalyst in a solvent and or diluent; recycling to the one or more comonomer synthesis reactors the unreacted ethylene monomer and the catalyst in a solvent and or diluent; and storing the comonomer for subsequent processing; wherein the comonomer is selected from the group consisting of 1-butene, 1-hexene, 1-octene, 1-decene and mixtures thereof.

Another aspect of the present disclosure relates to an advantageous method for preparing linear alpha olefin comonomers from ethylene monomer, which comprises the following steps: providing a combination comonomer synthesis reactor and gas/liquid phase separator into a single vessel; feeding an ethylene monomer, and a catalyst in a solvent and or diluent to the combination comonomer synthesis reactor and gas/liquid phase separator; reacting in the combination comonomer synthesis reactor and gas/liquid phase separator the ethylene monomer and the catalyst in solvent and or diluent under reaction conditions to produce an effluent stream comprising a gas stream of unreacted ethylene monomer and a liquid stream of comonomer and catalyst in a solvent and or diluent; recycling to the combination comonomer synthesis reactor and gas/liquid phase separator the gas stream and a portion of the liquid stream; and storing a remaining portion of the liquid stream for subsequent processing of the comonomer; wherein the comonomer is selected from the group consisting of 1-butene, 1-hexene, 1-octene, 1-decene and mixtures thereof.

Numerous advantages result from the advantageous method of preparing linear alpha olefin comonomers from ethylene monomer disclosed herein and the uses/applications therefore.

For example, in exemplary embodiments of the present disclosure, the disclosed method for preparing 1-butene, 1-hexene and other linear alpha olefin comonomers from ethylene monomer provides for substantial capital and operational cost savings over a conventional standalone process for manufacturing comonomer.

In a further exemplary embodiment of the present disclosure, the disclosed method for preparing 1-butene, 1-hexene and other linear alpha olefin comonomers from ethylene monomer provides for a simpler process through the elimination of one or more separation columns.

In a further exemplary embodiment of the present disclosure, the disclosed method for preparing 1-butene, 1-hexene and other linear alpha olefin comonomers from ethylene monomer provides for the capability to produce both 1-butene and 1-hexene through catalyst selection.

In a further exemplary embodiment of the present disclosure, the disclosed method for preparing linear alpha olefin comonomers from ethylene monomer provides for high selectivity and activity through trimerization catalyst selection.

In a further exemplary embodiment of the present disclosure, the disclosed method for preparing linear alpha olefin comonomers from ethylene monomer eliminates the need to recover unreacted ethylene monomer in high purity.

In a further exemplary embodiment of the present disclosure, the disclosed method for preparing linear alpha olefin comonomers from ethylene monomer permits the discharge of deactivated catalyst with comonomer product.

These and other advantages, features and attributes of the disclosed method for preparing 1-butene, 1-hexene and other linear alpha olefin comonomers from ethylene monomer of the present disclosure and their advantageous applications and/or uses will be apparent from the detailed description which follows, particularly when read in conjunction with the figures appended hereto.

BRIEF DESCRIPTION OF THE DRAWINGS

To assist those of ordinary skill in the relevant art in making and using the subject matter hereof, reference is made to the appended drawings, wherein.

DETAILED DESCRIPTION OF THE INVENTION

Figure 1:
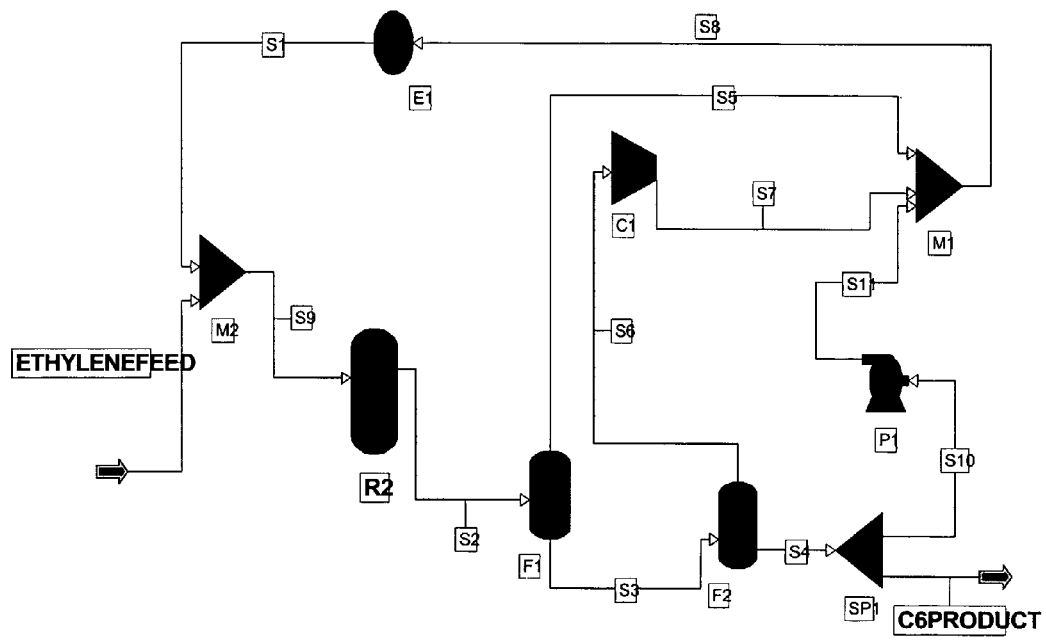
FIG. 1 depicts an exemplary process schematic of the process of the present invention for generating 1-hexene with 1-hexene as a solvent and or diluent.

For the purposes of this invention and the claims thereto when an oligomeric material (such as a dimer, trimer, or tetramer) is referred to as comprising an olefin, the olefin present in the material is the reacted form of the olefin. Likewise, the active species in a catalytic cycle may comprise the neutral or ionic forms of the catalyst. In addition, a reactor is any container(s) in which a chemical reaction occurs.

As used herein, the new numbering scheme for the Periodic Table Groups is used as set out in CHEMICAL AND ENGINEERING NEWS, 63(5), 27 (1985).

For purposes of this invention, a catalyst system is defined to be the combination of an activator and a metal ligand complex or the combination of an activator, a ligand and a metal precursor. A metal ligand complex is defined to be the product of the combination of a metal precursor and a ligand.

The phrase "optionally substituted" means that a moiety (such as a hydrocarbyl) may or may not be substituted. The term "substituted" means that at least one hydrogen atom bound to a carbon atom is replaced with a heteroatom containing group or a hydrocarbyl group. Further when the term "substituted" or "optionally substituted" introduces a list of possible substituted groups, it is intended that the term apply to every member of that group. That is, the phrase "substituted alkyl, alkenyl and alkynyl" is to be interpreted as "substituted alkyl, substituted alkenyl and substituted alkynyl." Similarly, "optionally substituted alkyl, alkenyl and alkynyl" is to be interpreted as "optionally substituted alkyl, optionally substituted alkenyl and optionally substituted alkynyl."

The term "hydrocarbyl" as used herein refers to hydrocarbyl radicals containing 1 to 50 carbon atoms. Preferred hydrocarbyls contain 1 to 24 carbon atoms, more specifically 1 to 16 carbon atoms, including branched or unbranched, cyclic or acyclic, saturated or unsaturated species, such as alkyl groups, alkenyl groups, aryl groups, and the like.

Throughout this specification, the presence of one solid line and one dashed line between any pair of atoms is intended to indicate that the bond in question may be a single bond or a double bond, or a bond with bond order intermediate between single and double, such as the delocalized bonding in an aromatic ring.

Certain abbreviations used herein are as follows: "i-Pr" to refer to isopropyl; "t-Bu" to refer to tertiary-butyl; "i-Bu" to refer to isobutyl; "Me" to refer to methyl; "Et" to refer to ethyl; "Ph" to refer to phenyl; "Mes" to refer to mesityl (2,4,6-trimethyl phenyl); "TFA" to refer to trifluoroacetate; "THF" to refer to tetrahydrofuran; "TMA" to refer to $AlMe_3$; "TIBA" to refer to $Al(i-Bu)_3$, and "acac" to refer to acetylacetonate.

The present invention relates to an improved process for generating long-chain linear alpha olefin comonomers (e.g. 1-butene, 1-hexene, 1-octene) from ethylene monomer using specific catalysts and/or catalyst systems as described below. The disclosed method of preparing 1-butene, 1-hexene and other linear alpha olefin comonomers from ethylene monomer prior to the polymerization reactor or other chemical process where it will be used greatly simplifies the comonomer synthesis process. A novel feature of the disclosed method of preparing 1-butene, 1-hexene and other linear alpha olefin comonomers from ethylene monomer is that ethylene is not recovered in high purity, which eliminates the need for a cryogenic distillation column and the associated capital and operating costs. Unconverted ethylene may then be recycled to the comonomer synthesis reactor, or sent on to another process, for example, a subsequent polyethylene polymerization process.

Another advantage of the method of the instant invention of preparing 1-butene, 1-hexene and other linear alpha olefin comonomers from ethylene monomer is that an elaborate on-site catalyst separation and disposal is not needed because the residual catalyst may pass with the comonomer for subsequent processing. A further advantage of the method of the instant invention of preparing 1-butene, 1-hexene and other linear alpha olefin comonomers from ethylene monomer is that a small amount of a soluble or slurry catalyst that is sufficiently active may be utilized, such that it can be added in only small amounts. After deactivation, the catalyst can then be discharged with the comonomer product and incorporated into the final polymeric product.

In one exemplary embodiment, the comonomer synthesis reactor is separate from the gas/liquid phase separator, which permits independent control of reaction and separation conditions. In this particular embodiment, ethylene and catalyst in a solvent and or diluent are fed separately to a comonomer synthesis reactor. The purity of the ethylene monomer feed may vary, but is preferably greater than 80% ethylene, more preferably greater than 99% ethylene, and even more preferably greater than 99.8% pure. The reactor temperature and pressure are controlled to provide for acceptable reaction rates and selectivities, as well as to provide for phase separation.

This invention further relates to processes for selectively oligomerizing (e.g., trimerizing and/or tetramerizing) $C_2$ to $C_{12}$ olefins, specifically ethylene, comprising reacting a catalytic composition or compound(s), optionally with one or more activators, with the olefin in the process described herein. As referred to herein, selective oligomerization refers to producing the desired oligomer with a selectivity of the reaction being at least 70%, more specifically at least 80% by mole of oligomer, with the possibility that an acceptable amount of polymer is present, but with the preference that no polymer is present in the product. In other embodiments, less than 20 weight % of polymer is present, specifically less than 5 weight %, more specifically less than 2 weight %, based upon the total weight of monomer converted to oligomers and polymers, where a polymer is defined to mean a molecule comprising more than 100 mers. In other embodiments, selective oligomerization refers to producing two desired oligomers, with the selectivity of the two desired oligomers summing to at least 80% by sum of mole of oligomers.

In another embodiment, this invention further relates to a method to trimerize or tetramerize a $C_2$ to $C_{12}$ olefin in the processes described herein wherein the method produces at least 70% selectivity for the desired oligomer(s) (specifically at least 80%, specifically at least 85%, specifically at least 90%, specifically at least 95%, specifically at least 98%, specifically at least 99%, specifically 100%), calculated based upon the amount of the desired oligomer produced relative to the total yield; and at least 70% of the olefin monomer reacts to form product (specifically at least 80%, specifically at least 85%, specifically at least 90%, specifically at least 95%, specifically at least 98%, specifically at least 99%, specifically 100%).

In another embodiment, this invention relates to a process to trimerize or tetramerize a $C_2$ to $C_{12}$ olefin (preferably ethylene) wherein the process produces at least 70% selectivity for the desired oligomer(s) (specifically at least 80%, specifically at least 85%, specifically at least 90%, specifically at least 95%, specifically at least 98%, specifically at least 99%, specifically 100%), calculated based upon the amount of the desired oligomer produced relative to the total yield; and at least 70% of the olefin monomer reacts to form product (specifically at least 80%, specifically at least 85%, specifically at least 90%, specifically at least 95%, specifically at least 98%, specifically at least 99%, specifically 100%).

A particularly useful catalyst system for selective oligomerization in the process described herein is formed from the combination of:

1) a ligand characterized by the following general formula:

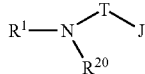

wherein:

$R^1$ and $R^{20}$ are each independently selected from the group consisting of consisting of hydrogen and optionally substituted hydrocarbyl, heteroatom containing hydrocarbyl and silyl (alternately $R^1$ and $R^{20}$ are each independently selected from the group consisting of: hydrogen and optionally substituted alkyl, heteroalkyl, cycloalkyl, heterocycloalkyl, aryl, heteroaryl, silyl and combinations thereof), provided that $R^1$ or $R^{20}$ do not equal T-J (alternately $R^1$ and $R^{20}$ are each independently a ring having from 4 to 8 atoms in the ring selected from the group consisting of substituted cycloalkyl, heterocycloalkyl, aryl and heteroaryl);

T is a bridging group, preferably represented by the formula -(T'$R^2R^3$)—, where T' is carbon or silicon, $R^2$ and $R^3$ are, each independently selected from the group consisting of hydrogen, halogen, and optionally substituted alkyl, heteroalkyl, aryl, heteroaryl, alkoxy, aryloxy, silyl, boryl, phosphino, amino, alkylthio, arylthio, and combinations thereof, provided that two or more $R^2$ and/or $R^3$ groups may be joined together to form one or more optionally substituted ring systems having from 3 to 50 non-hydrogen atoms (for example, T is cyclopropyl, where T'=C, and $R^2$ and $R^3$ together form —$CH_2$—$CH_2$—; or T is cyclohexyl, where T'=C and the two $R^2$ groups together form —$CH_2$—$CH_2$—$CH_2$—$CH_2$—);

J is an optionally substituted six-membered heterocycle, containing at least one nitrogen atom as part of the ring, or J is an optionally substituted five-membered heterocycle, containing at least one nitrogen atom as part of the ring;

2) a metal precursor compound characterized by the general formula $Cr(L)_n$ where each L is independently selected from the group consisting of halide, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, ether, thioether, carboxylates, thio, 1,3-dionates, oxalates, carbonates, nitrates, sulfates, ethers, thioethers and combinations thereof, wherein two or more L groups may be combined in a ring structure having from 3 to 50 non-hydrogen atoms; and n is 1, 2, 3, 4, 5, or 6; and 3) optionally, one or more activators.

In one embodiment, the ligand, as shown above, can be characterized by the following general formula, where J is a pyridyl or substituted pyridyl group:

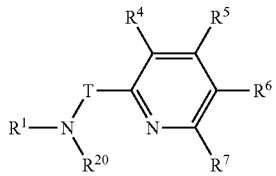

where $R^1$, $R^{20}$, and T are as described above; and $R^4$, $R^5$, $R^6$ and $R^7$ are independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof, and optionally two or more $R^1$, $R^{20}$, $R^2$, $R^3$, $R^4$, $R^5$, $R^6$ and $R^7$ groups may be joined to form one or more optionally substituted ring systems.

In another embodiment, the ligand can be characterized by the following general formula:

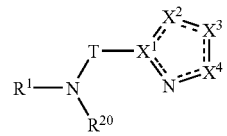

where $R^1$, $R^{20}$, and T are as described above; and $X^1$ is nitrogen or —$C(R^8)_{n''}$—, $X^2$, $X^3$, and $X^4$ are selected from the group consisting of oxygen, sulfur, —$C(R^8)_{n'}$—, —$N(R^8)_{n''}$—, and provided that at least one of $X^1$, $X^2$, $X^3$, or $X^4$ is carbon or —$C(R^8)_{n'}$—; each n' can be 1 or 2 and each n'' can be 0 or 1; and, each $R^8$ can be independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof, and optionally two or more $R^1$, $R^{20}$, $R^2$, $R^3$, and $R^8$ groups may be joined to form one or more optionally substituted ring systems.

In one embodiment, $R^1$ and $R^{20}$ are each independently selected from the group consisting of hydrogen and optionally substituted alkyl, heteroalkyl, aryl, heteroaryl, silyl and combinations thereof. In another embodiment, $R^1$ and $R^{20}$ are each independently a ring having from 4 to 8 atoms in the ring generally selected from the group consisting of substituted cycloalkyl, heterocycloalkyl, aryl, and heteroaryl.

In another embodiment (including all those described above), $R^{20}$ is hydrogen and $R^1$ is selected from the group consisting of alkyl, substituted alkyl, aryl, and substituted aryl.

In still another embodiment (including all those described above), $R^1$ and $R^{20}$ can each be independently selected from hydrogen and optionally substituted alkyl groups.

In yet another embodiment (including all those described above), $R^1$ and $R^{20}$ are joined in a ring structure having from 3 to 50 non-hydrogen atoms.

In another embodiment (including all those described above), $R^1$ is not hydrogen when $R^{20}$ is a cyclic group.

In still another embodiment (including all those described above), $R^{20}$ is not a hydrogen when $R^1$ is a cyclic group.

In another embodiment (including all those described above), $R^7$ is selected from the group consisting of optionally substituted aryl and heteroaryl.

In another embodiment (including all those described above), $R^2$ is hydrogen, and $R^3$ is selected from the group consisting of aryl, substituted aryl, heteroaryl, substituted heteroaryl, alkyl and substituted alkyl groups, and —$PY_2$ where Y is selected from the group consisting of aryl, substituted aryl, heteroaryl, and substituted heteroaryl.

In some embodiments (including all those described above), $R^1$ is hydrogen and $R^{20}$ is selected from the group consisting of methyl, ethyl, propyl, butyl, pentyl, hexyl, octyl, decyl, docecyl, benzyl, and —$CH_2CH_2Ph$ groups.

In some embodiments (including all those described above), $R^1$ and $R^{20}$ are each independently selected from the group consisting of methyl, ethyl, propyl, butyl, pentyl, hexyl, octyl, decyl, docecyl, benzyl and —CH$_2$CH$_2$Ph groups.

In some embodiments (including all those described above), R$^5$ is selected from the group consisting of —CF$_3$, H, F, Cl, —N(Me)$_2$ and —OR, wherein R is an optionally substituted alkyl group, an optionally substituted benzyl group or an optionally substituted aryl group.

In some embodiments (including all those described above), R$^3$ is selected from the group consisting of hydrogen and optionally substituted alkyl, heteroalkyl, cycloalkyl, heterocycloalkyl, silyl and combinations thereof.

The heterocycle-amine ligands, such as, pyridyl-amine ligands, described herein can be prepared according to the procedures known to those of ordinary skill in the art, for example, as described in U.S. Pat. Nos. 6,750,345; 6,713,577, and as described in U.S. Pat. Nos. 7,414,006, and 7,425,661, which are incorporated by reference herein.

Preferred ligands for use herein include pyridyl-amine ligands A1-A75 as seen in the attached figures, especially ligands A4, A5, A23, A28, A29, A30, and A38.

Preferred ligands useful herein also include those represented by the following formulae:

B1

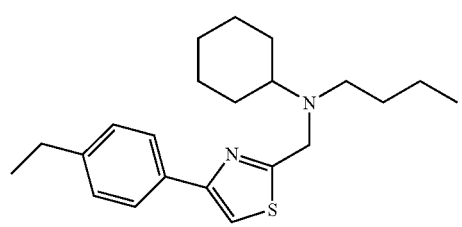

B2

B3

C1
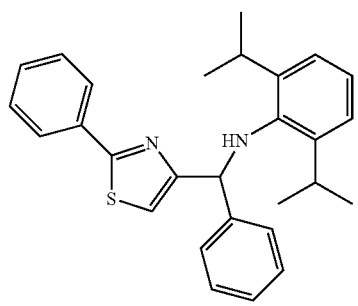

C2
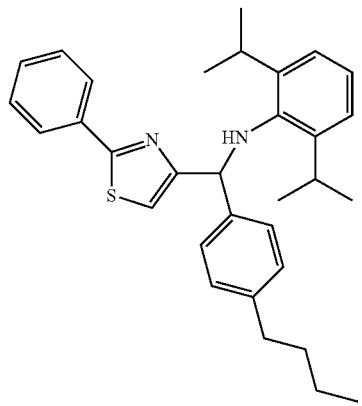

C3
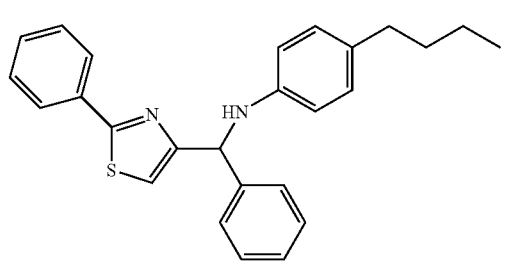

C4
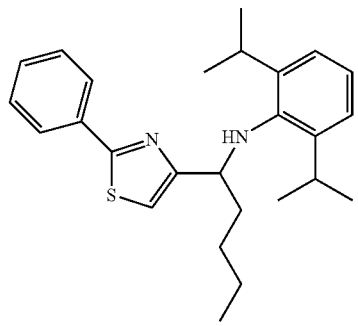

C5
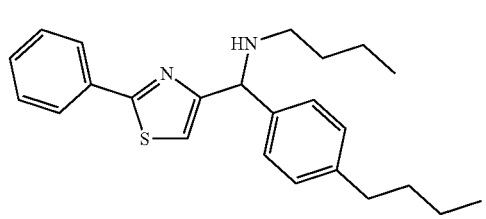

D1
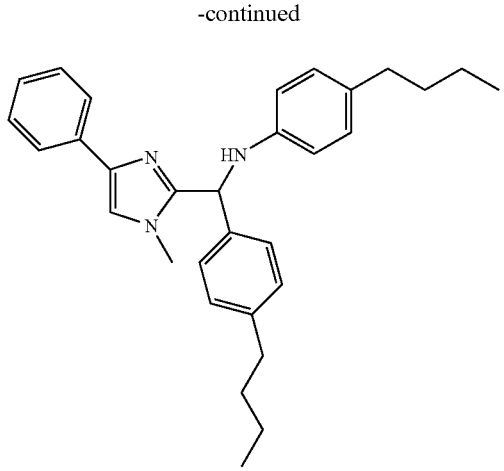
D2
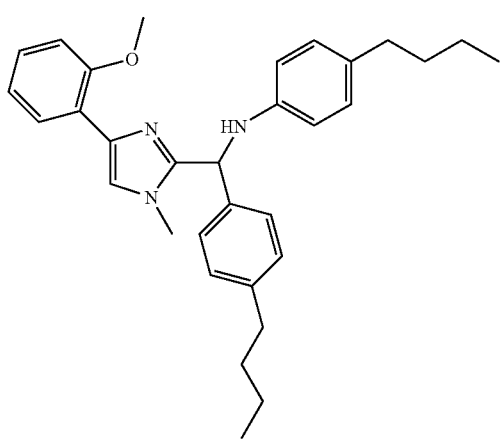
D3
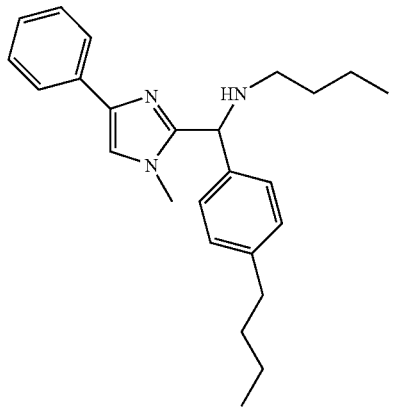
D4
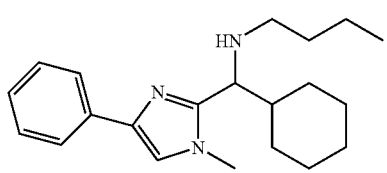
E1
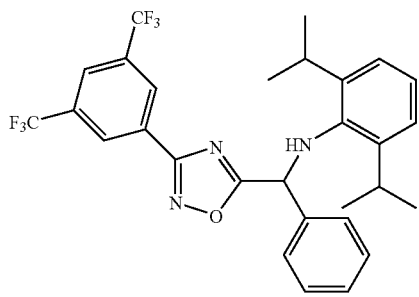
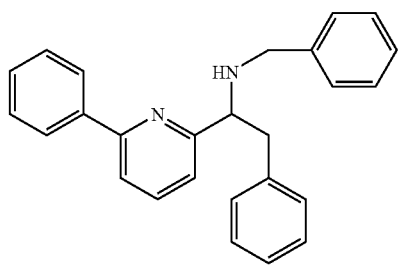
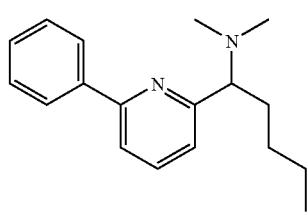
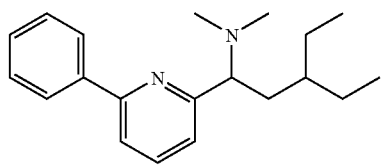
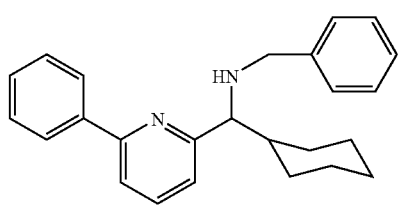
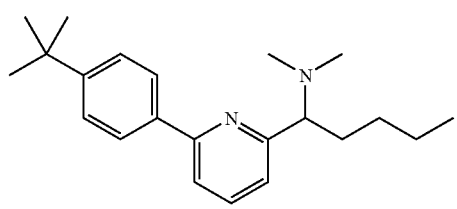
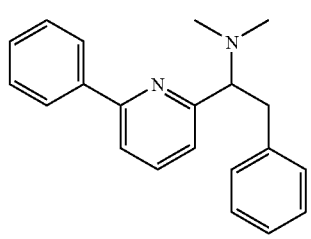

-continued

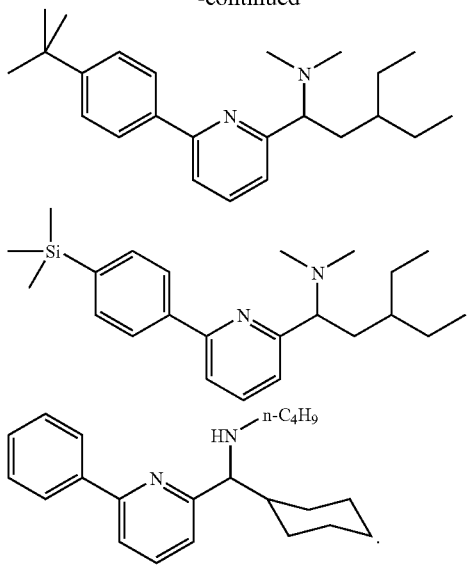

Particularly useful trimerization ligands useful herein include:

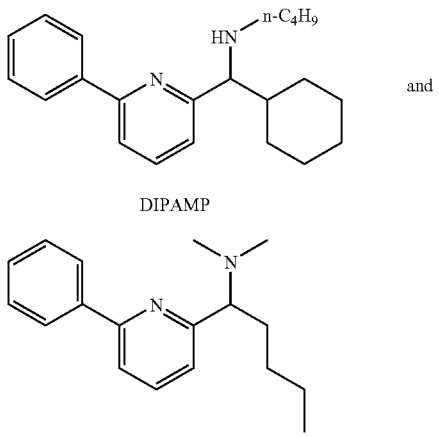

DIPAMP

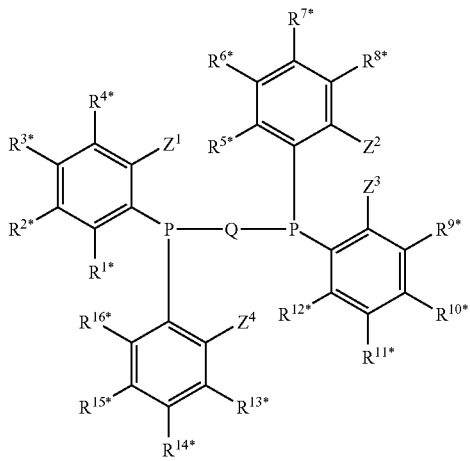

Another useful catalyst and or catalyst system for oligomerization of olefins (preferably the trimerization or tetramerization of C2 to C12 olefins, such as ethylene) useful herein is formed from the combination of:
1) at least one ligand represented by the formula:

wherein
P is phosphorus;
each of $R^{1*}$, $R^{2*}$, $R^{3*}$, $R^{4*}$, $R^{5*}$, $R^{6*}$, $R^{7*}$, $R^{8*}$, $R^{9*}$, $R^{10*}$, $R^{11*}$, $R^{12*}$, $R^{13*}$, $R^{14*}$, $R^{15*}$, and $R^{16*}$ is, independently, selected from the group consisting of hydrogen, halogen, optionally substituted hydrocarbyl and optionally substituted heteroatom containing hydrocarbyl;
each of $Z^1$, $Z^2$, $Z^3$ or $Z^4$ is, independently, selected from a first group consisting of hydrogen, a hydrocarbyl, alkoxy, aryloxy, alkylthio, arylthio, hydroxyl, mercapto and amino, (preferably at least two and less than all four of $Z^1$, $Z^2$, $Z^3$ or $Z^4$ is selected from a second group consisting of alkoxy, aryloxy, alkylthio, arylthio, hydroxyl, mercapto and amino; in alternate embodiments, $Z^1$, $Z^2$, $Z^3$ and $Z^4$ may not all be methoxy; in still further embodiments, either of the pairs of $Z^1$ and $Z^2$ or $Z^3$ and $Z^4$ are not both selected from the second group);
Q is a bridging group selected from the group consisting of optionally substituted hydrocarbyl having from 2 to 20 carbon atoms;
2) a metal precursor characterized by the general formula $Cr(L)_n$ where each L is independently selected from the group consisting of halide, alkyl, substituted alkyl, cycloalkyl, substituted cycloalkyl, heteroalkyl, substituted heteroalkyl heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, ether, thioether, carboxylates, thio, 1,3-dionates, oxalates, carbonates, nitrates, sulfates, ethers, thioethers and combinations thereof, and wherein two or more L groups may be combined in a ring structure having from 3 to 50 non-hydrogen atoms; n is 1, 2, 3, 4, 5, or 6; and
3) optionally, one or more activators.

In alternate embodiments, Q can be a hydrocarbyl bridge formed by an aryl or cycloalkyl group. For example, such aryl or cycloalkyl bridging groups include phenyl, naphthyl, biphenyl and cyclohexyl. In certain embodiments, the phosphorus atoms are connected apart from each other by two, three, four, five or six carbon bonds. For example, when a phenyl or cyclohexyl group is Q, the phosphorus atoms can be attached 1, 2 or 1, 3 or 1, 4 relative to each other (ortho, meta or para).

In some embodiments, when $Z^1$, $Z^2$, $Z^3$ or $Z^4$ are each methoxy and Q is an ethylene or methylene bridge, the metal precursor is not $CrCl_3(THF)_3$;

In another alternate embodiment, three of $Z^1$, $Z^2$, $Z^3$ or $Z^4$ are, independently, selected from the group consisting alkoxy, aryloxy, alkylthio, arylthio, hydroxyl, mercapto and amino and one of $Z^1$, $Z^2$, $Z^3$ or $Z^4$ is, independently, selected from the group consisting of hydrogen and hydrocarbyl.

In another alternate embodiment, each of $Z^1$, $Z^2$, $Z^3$ or $Z^4$ is, independently, selected from the group consisting alkoxy, aryloxy, alkylthio, arylthio, hydroxyl, mercapto and amino further provided that $Z^1$, $Z^2$, $Z^3$ and $Z^4$ may not all be methoxy.

In some embodiments $Z^1$, $Z^2$, $Z^3$ and $Z^4$ are, independently selected from the group consisting of methoxy, ethoxy, propoxy, isopropoxy, butoxy, isobutoxy, tert-butoxy, pentoxy, phenoxy, methylthio, ethylthio, propylthio, isopropylthio, butylthio, isobutylthio, tert-butylthio, phenylthio, dimethylamino, diethylamino, dipropylamino, diisopropylamino, dibutylamino, diisobutylamino, hydroxyl, and mercapto.

In some embodiments Q has from 2 to 16 carbon atoms, preferably Q is selected from the group consisting of ethyl, propyl, butyl, pentyl, hexyl, cyclohexyl, aryl, heptyl, tolyl, octyl, nonyl, decyl, phenyl, naphthyl, and dodecyl. In some embodiments each of $R^{1*}$, $R^{2*}$, $R^3$, $R^{4*}$, $R^{5*}$, $R^{6*}$, $R^{7*}$, $R^{8*}$, $R^{9*}$, $R^{10*}$, $R^{11*}$, $R^{12*}$, $R^{13*}$, $R^{14*}$, $R^{15*}$, and $R^{16*}$ is, independently, selected from the group consisting of hydrogen, a hydrocarbyl group having 1 to 20 carbon atoms, a substituted hydrocarbyl group having 1 to 20 carbon atoms and halogen. In some embodiments each of $Z^1$, $Z^2$, $Z^3$ or $Z^4$ is, independently, hydrogen, alkoxy, aryloxy, alkylthio, arylthio, hydroxyl, mercapto, amino, with the alkyl or aryl or substituents on these groups are a $C_1$ to $C_{20}$ hydrocarbyl group, preferably the $C_1$ to $C_{20}$ hydrocarbyl group is selected from the group consisting of methyl, ethyl, propyl, butyl, pentyl, hexyl, cyclohexyl, aryl, heptyl, tolyl, octyl, nonyl, decyl, phenyl, napthyl, benzyl, tolyl, or dodecyl.

In a preferred embodiment, one, two, three or all four of $Z^1$, $Z^2$, $Z^3$ or $Z^4$ are selected from the group consisting of alkoxy, aryloxy, alkylthio, arylthio, hydroxyl, mercapto, and amino. In another preferred embodiment, one, two, three or all four of $Z^1$, $Z^2$, $Z^3$ or $Z^4$ are an alkoxy, preferably methoxy.

A specific group of ligands useful in this invention include those represented by the formulae:

A1

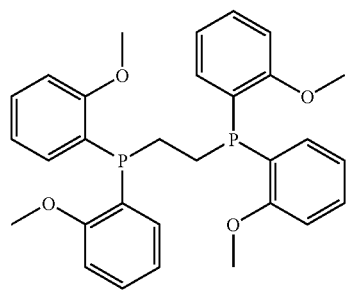

A2

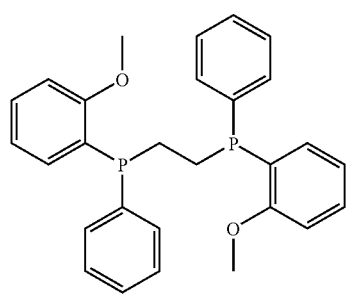

A3

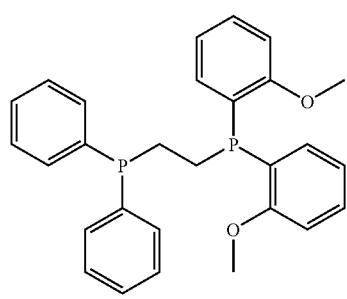

A4

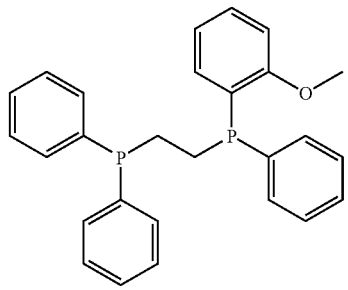

A5

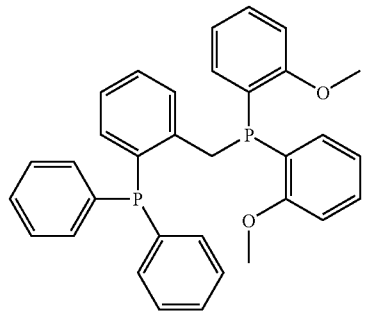

A6

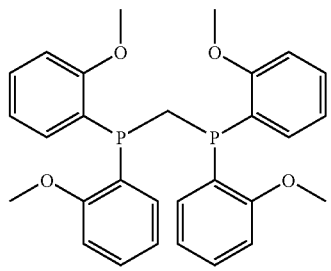

A7

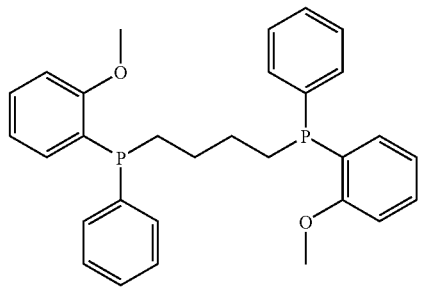

A8

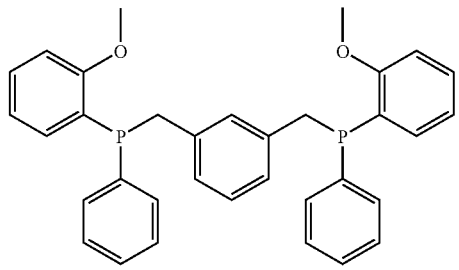

-continued

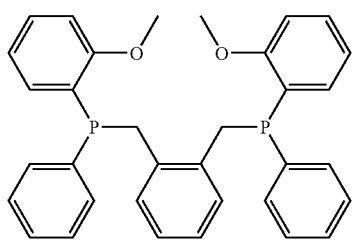

A9

A particularly preferred ligand is Ar$_2$PCH$_2$CH$_2$P(2-MeOPh)$_2$, wherein Ar is arene, Me is methyl, Ph is phenyl. Another preferred ligand is (ortho-methoxyphenyl)$_2$P—CH$_2$—CH$_2$—P(ortho-methoxyphenyl)$_2$.

Methods to prepare such ligands are discussed in U.S. Ser. No. 11/844,562, filed Aug. 24, 2007 assigned to ExxonMobil Chemical Patents Inc.

In certain embodiments when the catalyst precursor is CrCl$_3$(THF)$_3$, the ligand is not A1 or A6. Alternately in some embodiments, when the catalyst precursor is CrCl$_3$(THF)$_3$, the ligand is A1 or A6, then the activator is modified methylalumoxane ("MMAO") and or methylalumoxane ("MAO").

More specific ligands useful in the invention include: Ar$_2$PCH$_2$CH$_2$P(2-MeOPh)$_2$, where Ar is arene (in particular Ar is Ph, 2-MePh, 2,6-Me2Ph, 2,4,6-Me3Ph, 1-Naphthyl, or 2-Naphthyl), Me is methyl, Ph is phenyl.

Where asymmetric substitution at the phosphine leads a chiral center, pure enantiomers, pure diastereomers, or mixtures thereof may be used.

Metal Precursor

Once the desired ligand is formed, it can be combined with a Cr atom, ion, compound or other Cr precursor compound, and in some embodiments the present invention encompasses compositions that include any of the above-mentioned ligands in combination with an appropriate Cr precursor and an optional activator. Particularly useful Cr metal precursor compounds are represented by the formula Cr(L)$_n$ where L is an organic group, an inorganic group, or an anionic atom; and n is an integer of 1 to 6, and when n is not less than 2, L may be the same or different from each other. Each L is a ligand independently selected from the group consisting of hydrogen, halogen, optionally substituted alkyl, heteroalkyl, allyl, diene, alkenyl, heteroalkenyl, alkynyl, heteroalkynyl, aryl, heteroaryl, alkoxy, aryloxy, boryl, silyl, amino, phosphino, ether, thioether, phosphine, amine, carboxylate, alkylthio, arylthio, 1,3-dionate, oxalate, carbonate, nitrate, sulfate, and combinations thereof. Optionally, two or more L groups are joined into a ring structure. One or more of the ligands L may be ionically bonded to Cr and, for example, L may be a non-coordinated or loosely coordinated or weakly coordinated anion (e.g., L may be selected from the group consisting of those anions described below in the conjunction with the activators). See Marks et al., *Chem. Rev.* 100, pp 1391-1434 (2000) for a detailed discussion of these weak interactions. The chromium precursors may be monomeric, dimeric or higher orders thereof.

In a preferred embodiment, each L is independently a hydrocarbyl, halide, alkoxy, carboxylate, diaonate, amino, ether, or amine. In an alternate embodiment, each L is independently chloride, mesityl, tetrahydrofuran, methyl, ethyl, butyl, pentyl, hexyl, octyl, phenyl, Et$_2$O, NH$_3$, NMe$_3$, acetylacetonate, 2-ethylhexanoate, neopentyl, SMe$_2$, CH$_2$—C$_6$H$_4$-o-NMe$_2$, trifluoroacetate, CH(SiMe$_3$)$_2$, p-tolyl, diisopropylamide, picolinate, or NO$_3$, where Et is ethyl, Me is methyl.

Specific examples of suitable chromium precursors include, but are not limited to (THF)$_3$CrMeCl$_2$, (Mes)$_3$Cr(THF), [{TFA}$_2$Cr(OEt$_2$)]$_2$, (THF)$_3$CrPh$_3$, CrCl$_3$(THF)$_3$, CrCl$_4$(NH$_3$)$_2$, Cr(NMe$_3$)$_2$Cl$_3$, CrCl$_3$, Cr(acac)$_3$, Cr(2-ethylhexanoate)$_3$, Cr(neopentyl)$_4$, Cr(CH$_2$—C$_6$H$_4$-o-NMe$_2$)$_3$, Cr(TFA)$_3$, Cr(CH(SiMe$_3$)$_2$)$_3$, Cr(Mes)$_2$(THF)$_3$, Cr(Mes)$_2$(THF), Cr(Mes)Cl(THF)$_2$, Cr(Mes)Cl(THF)$_{0.5}$, Cr(p-tolyl)Cl$_2$(THF)$_3$, Cr(diisopropylamide)$_3$, Cr(picolinate)$_3$, [Cr$_2$Me$_8$][Li(THF)]$_4$, CrCl$_2$(THF), Cr(NO$_3$)$_3$, [CrMe$_6$][Li(Et$_2$O)]$_3$ [CrPh$_6$][Li(THF)]$_3$, [CrPh$_6$][Li(n-Bu$_2$O)]$_3$, [Cr(C$_4$H$_8$)$_3$][Li(THF)]$_3$, and other well known chromium compounds commonly used as precursors in the formation of Cr complexes and catalysts.

Preferred metal precursors used herein can be selected from the group consisting of (THF)$_3$CrMeCl$_2$, (THF)$_3$CrCl$_3$, (Mes)$_3$Cr(THF), [{TFA}$_2$Cr(OEt$_2$)]$_2$, (THF)$_3$CrPh$_3$, and mixtures thereof.

The ligand may be mixed with a metal precursor compound prior to or simultaneously with allowing the mixture to be contacted with the reactants (e.g., monomers). The ligand to metal precursor compound ratio can be in the range of about 0.01:1 to about 100:1, more specifically in the range of about 0.1:1 to about 10:1.

Cr-ligand complexes can take a number of different coordination modes. General examples of possible coordination modes include those characterized by the following general formulas:

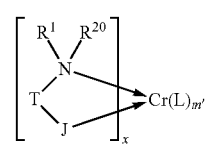

VI(a)

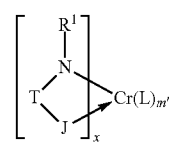

VI(b)

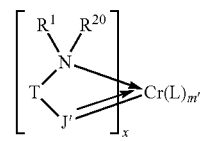

VI(c)

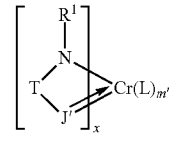

VI(d)

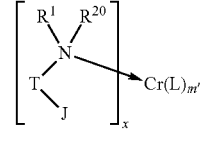

VI(e)

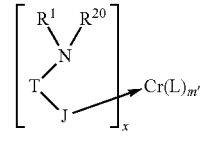

VI(f)

-continued

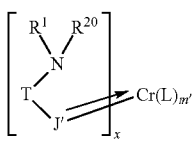

VI(g)

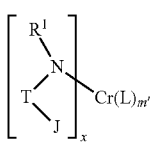

VI(h)

wherein $R^1$, $R^{20}$, L, J and T are described above; x is 1 or 2; and m' is 1, 2, 3, 4, or 5. J' is defined the same as J is defined above, provided that J' includes 2 atoms bonded to the Cr, one of the which is in the ring position adjacent to the atom bonded to T, which is bonded to Cr through a dative bond, and the other of which is bonded to the Cr through a covalent bond. Numerous other coordination modes are possible, for example the ligands may bind to two chromium metal centers in a bridging fashion (see for example Cotton and Walton, *Multiple Bonds Between Metal Atoms* 1993, Oxford University Press).

In some embodiments, the ligand will be mixed with a suitable metal precursor prior to or simultaneous with allowing the mixture to be contacted to the reactants. When the ligand is mixed with the metal precursor, a metal-ligand complex is formed. In connection with the metal-ligand complex and depending on the ligand or ligands chosen, the metal-ligand complex may take the form of dimers, trimers or higher orders thereof or there may be two or more metal atoms that are bridged by one or more ligands. Furthermore, two or more ligands may coordinate with a single metal atom. The exact nature of the metal-ligand complex(es) formed depends on the chemistry of the ligand and the method of combining the metal precursor and ligand, such that a distribution of metal-ligand complexes may form with the number of ligands bound to the metal being greater than, equal to or less than the number of equivalents of ligands added relative to an equivalent of metal precursor.

In one embodiment, the metal complex is represented by the formula:

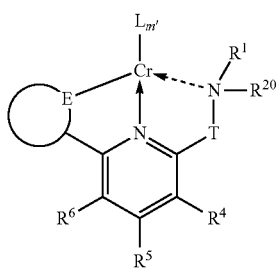

wherein $R^1$, $R^4$, $R^5$, $R^6$, $R^{20}$, T, L and m' are as described above; and E is a carbon atom that is part of an optionally substituted aryl or heteroaryl ring. In one aspect, the aryl or heteroaryl ring may be polycyclic.

Listed below are some examples of Cr-Ligand complex embodiments useful herein:

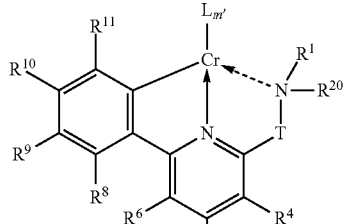

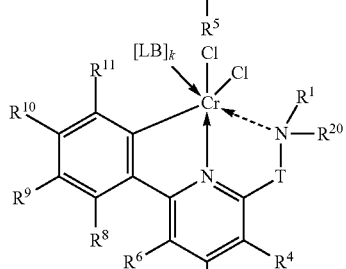

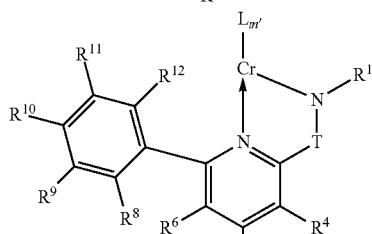

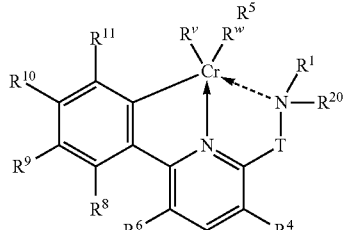

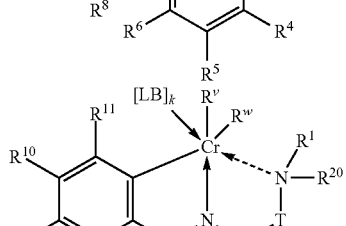

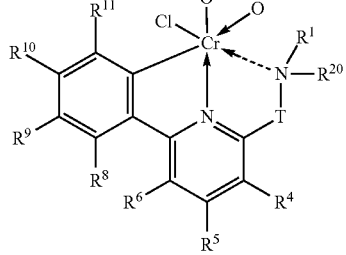

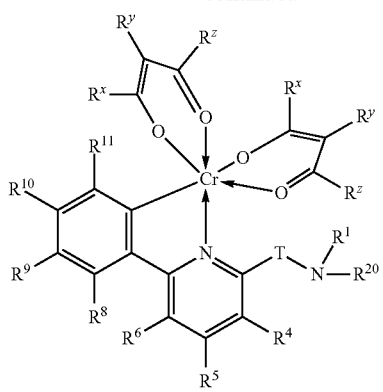

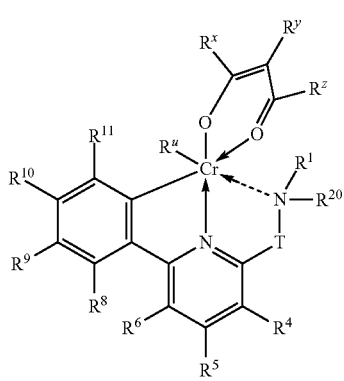

wherein $R^1$, $R^2$, $R^3$, $R^4$, $R^5$, $R^6$, $R^{20}$, T are as defined above;

$R^8$, $R^9$, $R^{10}$, $R^{11}$, and $R^{12}$ are independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof, and optionally two or more $R^8$ $R^9$, $R^{10}$, $R^{11}$ and $R^{12}$ groups may be joined to form one or more optionally substituted ring systems;

$R^u$, $R^v$, $R^w$, $R^x$, $R^y$ and $R^z$ are optionally substituted alkyl, heteroalkyl, aryl, heteroaryl;

L and m' are as defined above;

a dashed arrow indicates that the dative bond is an optional bond which may or may not be present; and LB is a Lewis base and k=0 or 1.

Some specific embodiments of Cr-Ligand complexes useful herein are shown below:

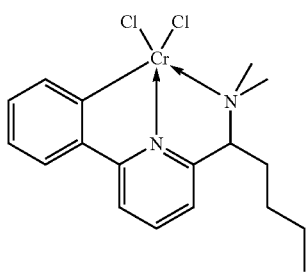

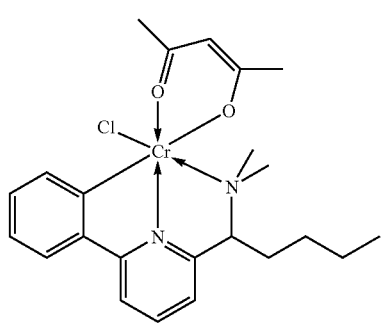

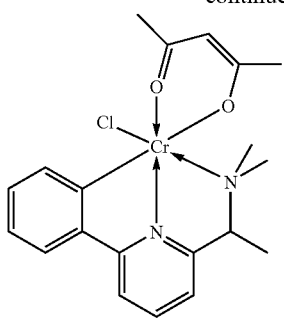

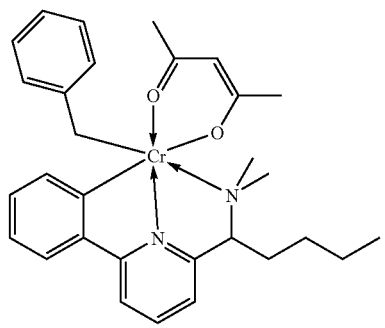

In still further embodiments, Cr-ligand complexes can take a number of different coordination modes. General examples of possible coordination modes include those represented by the formulae:

1

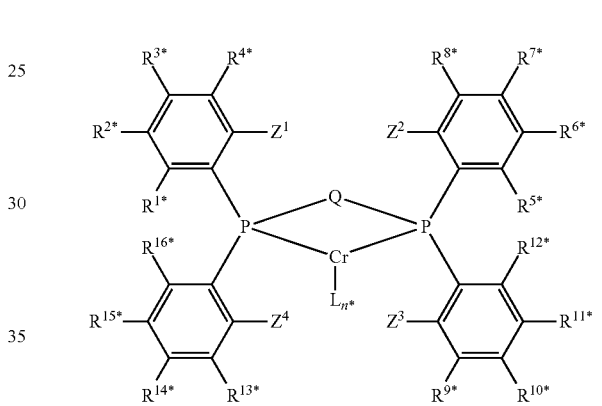

2

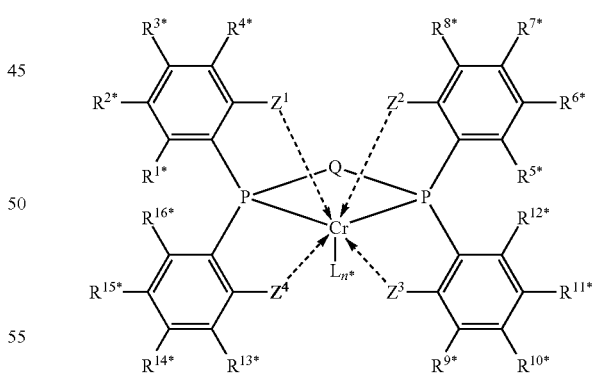

wherein n*=0, 1, 2, 3, or 4, and $R^{1*}$ to $R^{16*}$, Q, L, and $Z^1$ to $Z^4$ are as defined above. In a preferred embodiment of formula 2, any one or more of $Z^1, Z^2, Z^3$ and $Z^4$ may form a dative bond to the chromium. In certain circumstances, for instance, during catalysis, the formation of the dative bonds may be reversible. Further specific examples of Cr-ligand complexes useful in the invention are shown below:

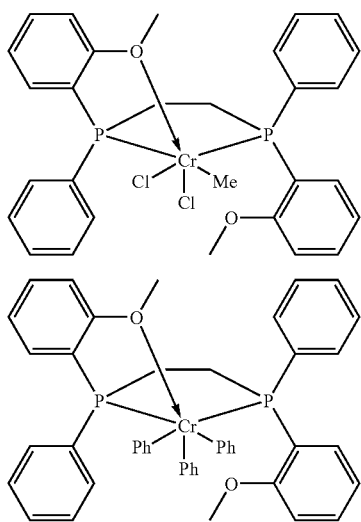

M1

M2

Further description of such complexes and how to prepare them is disclosed in U.S. Ser. No. 11/844,562, filed Aug. 24, 2007 assigned to ExxonMobil Chemical Patents Inc.

Activators

The ligand-metal-precursor combinations and the metal ligand complexes, described above, are optionally activated in various ways to yield compositions active for selective oligomerization (preferably ethylene oligomerization). For the purposes of this patent specification and appended claims, the terms "cocatalyst" and "activator" are used herein interchangeably and are defined to be any compound which can activate any one of the ligands-metal-precursor-combinations and the metal ligand complexes, described above by converting the combination, complex, or composition into a catalytically active species. Non-limiting activators, for example, include alumoxanes, aluminum alkyls, other metal or main group alkyl or aryl compounds, ionizing activators, which may be neutral or ionic, Lewis acids, reducing agents, oxidizing agents, and combinations thereof.

In one embodiment, alumoxane activators are utilized as an activator in the compositions useful in the invention. Alumoxanes are generally oligomeric compounds containing —Al(R*)—O— sub-units, where R* is an alkyl group. Examples of alumoxanes include methylalumoxane (MAO), ethylalumoxane, isobutylalumoxane, and modified methylalumoxanes (MMAO), which include alkyl groups other than methyl such as ethyl, isobutyl, and n-octyl, such as MMAO-3A, PMAO-IP (referring to polymethylalumoxane, improved process, manufactured by Akzo-Nobel and meaning an MAO prepared from a non-hydrolytic process). Alkylalumoxanes and modified alkylalumoxanes are suitable as catalyst activators, particularly when the abstractable ligand of the catalyst is a halide, alkoxide or amide. Mixtures of different alumoxanes and modified alumoxanes may also be used. For further descriptions on production and use of alumoxanes, see U.S. Pat. Nos. 4,665,208, 4,952,540, 5,041,584, 5,091,352, 5,206,199, 5,204,419, 4,874,734, 4,924,018, 4,908,463, 4,968,827, 5,329,032, 5,248,801, 5,235,081, 5,157,137, 5,103,031 and EP0561476A1, EP0279586B1, EP0516476A1, EP0594218A1 and WO94/10180.

When the activator is an alumoxane (modified or unmodified), some embodiments select the maximum amount of activator at a 5000-fold molar excess Al/Cr over the catalyst precursor. The minimum preferred activator-to-catalyst-precursor is a 1:1 molar ratio. More specifically, the Al/Cr ratio is from 1000:1 to 100:1.

It may be preferable to use a visually clear methylalumoxane. A cloudy or gelled alumoxane can be filtered to produce a clear solution or clear alumoxane can be decanted from the cloudy solution. Another particularly useful alumoxane is a modified methyl alumoxane (MMAO) cocatalyst type 3A (commercially available from Akzo Chemicals, Inc. under the trade name Modified Methylalumoxane type 3A, covered under U.S. Pat. No. 5,041,584).

Aluminum alkyl or organoaluminum compounds which may be utilized as activators (or scavengers) include trimethylaluminum, triethylaluminum, triisobutylaluminum, tri-n-hexylaluminum, tri-n-octylaluminum, diisobutylaluminum hydride, ethylaluminum dichloride, diethylaluminum chloride, diethylaluminum ethoxide and the like.

Ionizing Activators

In some embodiments, the activator includes compounds that may abstract a ligand making the metal complex cationic and providing a charge-balancing non-coordinating or weakly coordinating anion. The term "non-coordinating anion" (NCA) means an anion which either does not coordinate to said cation or which is only weakly coordinated to said cation thereby remaining sufficiently labile to be displaced by a neutral Lewis base.

It is within the scope of this invention to use an ionizing or stoichiometric activator, neutral or ionic, such as tri (n-butyl) ammonium tetrakis (pentafluorophenyl) boron, a tris(perfluorophenyl) boron metalloid precursor or a tris(perfluoronaphthyl) boron metalloid precursor, polyhalogenated heteroborane anions (WO98/43983), boric acid (U.S. Pat. No. 5,942,459) or combination thereof. It is also within the scope of this invention to use neutral or ionic activators alone or in combination with alumoxane or modified alumoxane activators.

Examples of neutral stoichiometric activators include tri-substituted boron, tellurium, aluminum, gallium and indium or mixtures thereof. The three substituent groups are each independently selected from alkyls, alkenyls, halogen, substituted alkyls, aryls, arylhalides, alkoxy and halides. In some embodiments, the three groups are independently selected from halogen, mono or multicyclic (including halosubstituted) aryls, alkyls, and alkenyl compounds and mixtures thereof, preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). In other embodiments, the three groups are alkyls having 1 to 4 carbon groups, phenyl, naphthyl or mixtures thereof. In further embodiments, the three groups are halogenated, specifically fluorinated, aryl groups. In even further embodiments, the neutral stoichiometric activator is tris(perfluorophenyl) boron or tris(perfluoronaphthyl) boron.

Ionic stoichiometric activator compounds may contain an active proton, or some other cation associated with, but not coordinated to, or only loosely coordinated to, the remaining ion of the ionizing compound. Such compounds and the like are described in European publications EP0570982A1, EP0520732A1, EP0495375A1, EP0500944B1, EP0277003A1 and EP0277004A1, and U.S. Pat. Nos. 5,153,157, 5,198,401, 5,066,741, 5,206,197, 5,241,025, 5,384,299 and 5,502,124 and U.S. patent application Ser. No. 08/285,380, filed Aug. 3, 1994, all of which are herein fully incorporated by reference.

Ionic catalysts can be prepared by reacting a Cr compound with some neutral Lewis acids, such as $B(C_6F_6)_3$, which upon reaction with the abstractable ligand (X) of the Cr compound forms an anion, such as ([B(C$_6$F$_5$)$_3$(X)]$^-$), which stabilizes the cationic Cr species generated by the reaction. The catalysts can be prepared with activator components which are ionic compounds or compositions.

In some embodiments, compounds useful as an activator component in the preparation of the ionic catalyst systems used in the process of this invention comprise a cation, which is optionally a Brönsted acid capable of donating a proton, and a compatible non-coordinating anion which is capable of stabilizing the active catalyst species which is formed when the two compounds are combined and said anion will be sufficiently labile to be displaced by olefinic substrates or other neutral Lewis bases such as ethers, nitriles and the like. Two classes of compatible non-coordinating anions useful herein have been disclosed in EP0277003A1 and EP0277004A1 published 1988: anionic coordination complexes comprising a plurality of lipophilic radicals covalently coordinated to and shielding a central charge-bearing metal or metalloid core; and, anions comprising a plurality of boron atoms such as carboranes, metallacarboranes and boranes.

In one preferred embodiment, the stoichiometric activators include a cation and an anion component, and may be represented by the following formula:

$$(L-H)_d^+(A^{d-})$$

where L is a neutral Lewis base; H is hydrogen; (L-H)$^+$ is a Brönsted acid; A$^{d-}$ is a non-coordinating anion having the charge d−; and d is an integer from 1 to 3. The cation component, (L-H)$_d^+$ may include Brönsted acids such as protons or protonated Lewis bases or reducible Lewis acids capable of protonating or abstracting a moiety, such as an alkyl or aryl, from the bulky ligand chromium catalyst precursor, resulting in a cationic transition metal species.

The activating cation (L-H)$_d^+$ may be a Brönsted acid, capable of donating a proton to the transition metal catalytic precursor resulting in a transition metal cation, including ammoniums, oxoniums, phosphoniums, silyliums, and mixtures thereof, specifically ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxoniums from ethers such as dimethyl ether diethyl ether, tetrahydrofuran and dioxane, sulfoniums from thioethers, such as diethyl thioethers and tetrahydrothiophene, and mixtures thereof. The activating cation (L-H)$_d^+$ may also be a moiety such as silver, tropylium, carbeniums, ferroceniums and mixtures, specifically carboniums and ferroceniums. In one embodiment (L-H)$_d^+$ can be triphenyl carbonium.

The anion component A$^{d-}$ includes those having the formula [M$^{k+}$Q$_n$]$^{d-}$ wherein k is an integer from 1 to 3; n is an integer from 2-6; n−k=d; M is an element selected from Group 13 of the Periodic Table of the Elements, specifically boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than 1 occurrence is Q a halide. Specifically, each Q is a fluorinated hydrocarbyl group having 1 to 20 carbon atoms, more specifically each Q is a fluorinated aryl group, and most specifically each Q is a pentafluoryl aryl group.

Examples of suitable A$^{d-}$ also include diboron compounds as disclosed in U.S. Pat. No. 5,447,895, which is fully incorporated herein by reference.

Illustrative, but not limiting examples of boron compounds which may be used as an activating cocatalyst herein are tri-substituted ammonium salts such as: trimethylammonium tetraphenylborate, triethylammonium tetraphenylborate, tripropylammonium tetraphenylborate, tri(n-butyl)ammonium tetraphenylborate, tri(t-butyl)ammonium tetraphenylborate, N,N-dimethylanilinium tetraphenylborate, N,N-diethylanilinium tetraphenylborate, N,N-dimethyl-(2,4,6-trimethylanilinium)tetraphenylborate, tropillium tetraphenylborate, triphenylcarbenium tetraphenylborate, triphenylphosphonium tetraphenylborate, triethylsilylium tetraphenylborate, benzene(diazonium)tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium) tetrakis (pentafluorophenyl)borate, tropillium tetrakis (pentafluorophenyl)borate, triphenylcarbenium tetrakis (pentafluorophenyl)borate, triphenylphosphonium tetrakis (pentafluorophenyl)borate, triethylsilylium tetrakis (pentafluorophenyl)borate, benzene(diazonium)tetrakis (pentafluorophenyl)borate, trimethylammonium tetrakis-(2, 3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluoro-phenyl)borate, dimethyl(t-butyl)ammonium tetrakis-(2,3,4,6-tetrafluorophenyl) borate, N,N-dimethylanilinium tetrakis-(2,3,4,6-tetrafluorophenyl)borate, N,N-diethylanilinium tetrakis-(2,3, 4,6-tetrafluorophenyl)borate, N,N-dimethyl-(2,4,6-trimethylanilinium)tetrakis-(2,3,4,6-tetrafluorophenyl) borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium)tetrakis-(2,3,4,6-tetrafluorophenyl)borate, trimethylammonium tetrakis (perfluoronaphthyl)borate, triethylammonium tetrakis (perfluoronaphthyl)borate, tripropylammonium tetrakis (perfluoronaphthyl)borate, tri(n-butyl)ammonium tetrakis (perfluoronaphthyl)borate, tri(t-butyl)ammonium tetrakis (perfluoronaphthyl)borate, N,N-dimethylanilinium tetrakis (perfluoronaphthyl)borate, N,N-diethylanilinium tetrakis (perfluoronaphthyl)borate, N,N-dimethyl-(2,4,6-trimethylanilinium)tetrakis(perfluoronaphthyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium) tetrakis (perfluoronaphthyl)borate, trimethylammonium tetrakis (perfluorobiphenyl)borate, triethylammonium tetrakis (perfluorobiphenyl)borate, tripropylammonium tetrakis (perfluorobiphenyl)borate, tri(n-butyl)ammonium tetrakis (perfluorobiphenyl)borate, tri(t-butyl)ammonium tetrakis (perfluorobiphenyl)borate, N,N-dimethylanilinium tetrakis (perfluorobiphenyl)borate, N,N-diethylanilinium tetrakis (perfluorobiphenyl)borate, N,N-dimethyl-(2,4,6-trimethylanilinium)tetrakis(perfluorobiphenyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium)tetrakis (perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(t-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium)tetrakis(3,5-bis(trifluoromethyl)phenyl)borate, tropillium tetrakis(3,5-bis(trifluoromethyl)phenyl)borate, triphenylcarbenium tetrakis(3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, benzene(diazonium)tetrakis(3,5-bis(trifluoromethyl)phenyl)borate, and dialkyl ammonium salts such as: di-(i-propyl)ammonium tetrakis(pentafluorophenyl)borate, and dicyclohexylammonium tetrakis(pentafluorophenyl)borate; and additional tri-substituted phosphonium salts such as tri(o-tolyl)phosphonium tetrakis(pentafluorophenyl)borate, and tri(2,6-dimethylphenyl)phosphonium tetrakis(pentafluorophenyl)borate.

Specifically useful ionic stoichiometric activators include: N,N-dimethylanilinium tetra(perfluorophenyl)borate, N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl) borate, triphenylcarbenium tetrakis(perfluoronaphthyl) borate, triphenylcarbenium tetrakis(perfluorobiphenyl) borate, triphenylcarbenium tetrakis(3,5-bis(trifluoromethyl) phenyl)borate, and triphenylcarbenium tetra (perfluorophenyl)borate.

Other examples of preferred ionizing activators include, $HNMe(C_{18}H_{37})_2{}^+B(C_6F_5)_4{}^-$; $HNPh(C_{18}H_{37})_2{}^+B(C_6F_5)_4{}^-$ and $((4\text{-}n\text{-}Bu\text{-}C_6H_4)NH(n\text{-}hexyl)_2)^+B(C_6F_5)_4{}^-$ and $((4\text{-}n\text{-}Bu\text{-}C_6H_4)NH(n\text{-}decyl)_2)^+B(C_6F_5)_4{}^-$. Specific preferred $(L^*-H)^+$ cations are N,N-dialkylanilinium cations, such as $HNMe_2Ph^+$, substituted N,N-dialkylanilinium cations, such as $(4\text{-}n\text{-}Bu\text{-}C_6H_4)NH(n\text{-}C_6H_{13})_2{}^+$ and $(4\text{-}n\text{-}Bu\text{-}C_6H_4)NH(n\text{-}C_{10}H_{21})_2{}^+$ and $HNMe(C_{18}H_{37})_2{}^+$. Specific examples of anions are tetrakis(3,5-bis(trifluoromethyl)phenyl)borate and tetrakis(pentafluorophenyl)borate.

In one embodiment, activation methods using ionizing ionic compounds not containing an active proton but capable of producing an active oligomerization catalyst are also contemplated. Such methods are described in relation to metallocene catalyst compounds in EP0426637A1, EP0573403A1 and U.S. Pat. No. 5,387,568, which are all herein incorporated by reference.

The process can also employ cocatalyst compounds or activator compounds that are initially neutral Lewis acids but form a cationic metal complex and a noncoordinating anion, or a zwitterionic complex upon reaction with the compounds of this invention. For example, tris(pentafluorophenyl) boron or aluminum may act to abstract a hydrocarbyl or hydride ligand to yield a cationic metal complex and stabilizing noncoordinating anion.

In some embodiments, ionizing activators may be employed as described in Köhn et al. (*J. Organomet. Chem.*, 683, pp 200-208, (2003)) to, for example, improve solubility.

In another embodiment, the aforementioned cocatalyst compounds can also react with the compounds to produce a neutral, uncharged catalyst capable of selective ethylene oligomerization. For example, Lewis acidic reagents such as, for example, alkyl or aryl aluminum or boron compounds, can abstract a Lewis basic ligand such as, for example, THF or $Et_2O$, from a compound yielding a coordinatively unsaturated catalyst capable of selective ethylene oligomerization.

When the cations of noncoordinating anion precursors are Brönsted acids such as protons or protonated Lewis bases (excluding water), or reducible Lewis acids such as ferrocenium or silver cations, or alkali or alkaline earth metal cations such as those of sodium, magnesium or lithium, the activator-to-catalyst-precursor molar ratio may be any ratio, however, useful ratios can be from 1000:1 to 1:1.

Combinations of two or more activators may also be used in the practice of this invention.

Another suitable ion forming, activating cocatalyst comprises a salt of a cationic oxidizing agent and a noncoordinating, compatible anion characterized by the general formula:

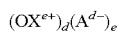

where $OX^{e+}$ is a cationic oxidizing agent having a charge of e+; e is an integer from 1 to 3; d is an integer from 1 to 3, and $A^{d-}$ is as previously defined. Examples of cationic oxidizing agents include: ferrocenium, hydrocarbyl-substituted ferrocenium, $Ag^+$, or $Pb^{+2}$. Preferred embodiments of $A^{d-}$ are those anions previously defined with respect to the Brönsted acid containing activators, especially tetrakis(pentafluorophenyl)borate.

Group 13 Reagents, Divalent Metal Reagents, and Alkali Metal Reagents

Other general activators or compounds useful in an oligomerization reaction may be used. These compounds may be activators in some contexts, but may also serve other functions in the reaction system, such as alkylating a metal center or scavenging impurities. These compounds are within the general definition of "activator," but are not considered herein to be ion-forming activators. These compounds include a group 13 reagent that may be characterized by the formula $G^{13}R^{50}{}_{3-p}D_p$ where G is selected from the group consisting of B, Al, Ga, In, and combinations thereof, p is 0, 1 or 2, each $R^{50}$ is independently selected from the group consisting of hydrogen, halogen, and optionally substituted alkyl, alkenyl, alkynyl, heteroalkyl, heteroalkenyl, heteroalkynyl, aryl, heteroaryl, and combinations thereof, and each D is independently selected from the group consisting of halogen, hydrogen, alkoxy, aryloxy, amino, mercapto, alkylthio, arylthio, phosphino and combinations thereof.

In other embodiments, a divalent metal reagent may be used that is characterized by the general formula $M'R^{50}{}_{2-p'}D_{p'}$ and p' is 0 or 1 in this embodiment and $R^{50}$ and D are as defined above. M' is the metal and is selected from the group consisting of Mg, Ca, Sr, Ba, Zn, Cd, Cu and combinations thereof.

In still other embodiments, an alkali metal reagent may be used that is defined by the general formula $M^{iv}R^{50}$ and in this embodiment $R^{50}$ is as defined above, and $M^{iv}$ is the alkali metal and is selected from the group consisting of Li, Na, K, Rb, Cs and combinations thereof. Additionally, hydrogen and/or silanes may be used in the catalytic composition or added to the polymerization system. Silanes may be characterized by the formula $SiR^{50}{}_{4-q}D_q$ where $R^{50}$ is defined as above, q is 1, 2, 3 or 4 and D is as defined above, with the proviso that at least one D is hydrogen.

Non-limiting examples of Group 13 reagents, divalent metal reagents, and alkali metal reagents useful as activators for the catalyst compounds described above include methyl lithium, butyl lithium, phenyl lithium, dihexylmercury, butylmagnesium, diethylcadmium, benzylpotassium, diethyl zinc, tri-n-butyl aluminum, diisobutyl ethylboron, diethylcadmium, di-n-butyl zinc and tri-n-amyl boron, and, in particular, the aluminum alkyls, such as trihexyl-aluminum, triethylaluminum, trimethylaluminum, and triisobutyl aluminum, diisobutyl aluminum bromide, diethylaluminum chloride, ethylaluminum dichloride, isobutyl boron dichloride, methyl magnesium chloride, ethyl beryllium chloride, ethyl calcium bromide, diisobutyl aluminum hydride, methyl cadmium hydride, diethyl boron hydride, hexylberyllium hydride, dipropylboron hydride, octylmagnesium hydride, butyl zinc hydride, dichloroboron hydride, di-bromo-aluminum hydride and bromocadmium hydride. Other Group 13 reagents, divalent metal reagents, and alkali metal reagents useful as activators for the catalyst compounds described above are known to those in the art, and a more complete discussion of these compounds may be found in U.S. Pat. Nos. 3,221,002 and 5,093,415, which are herein fully incorporated by reference.

Other activators include those described in PCT publication WO98/07515 such as tris(2,2',2"-nonafluorobiphenyl) fluoroaluminate, which publication is fully incorporated herein by reference. Combinations of activators are also contemplated by the invention, for example, alumoxanes and ionizing activators in combinations, see for example, EP0573120B1, PCT publications WO94/07928 and WO95/14044 and U.S. Pat. Nos. 5,153,157 and 5,453,410, all of which are herein fully incorporated by reference.

Other suitable activators are disclosed in WO98/09996, incorporated herein by reference, which describes activating bulky ligand metallocene catalyst compounds with perchlorates, periodates and iodates including their hydrates. WO98/30602 and WO98/30603, incorporated by reference, describe the use of lithium (2,2'-bisphenyl-ditrimethylsilicate).4THF as an activator for a bulky ligand metallocene catalyst compound. WO99/18135, incorporated herein by reference, describes the use of organo-boron-aluminum activators. EP0781299B1 describes using a silylium salt in combination with a non-coordinating compatible anion. Also, methods of activation such as using radiation (see EP0615981B1 herein incorporated by reference), electro-chemical oxidation, and the like are also contemplated as activating methods for the purposes of rendering the chromium complexes or compositions active for the selective oligomerization of olefins. Other activators or methods are described in for example, U.S. Pat. Nos. 5,849,852, 5,859,653 and 5,869,723 and WO98/32775, WO99/42467 (dioctadecylmethylammonium-bis(tris(pentafluorophenyl)borane) benzimidazolide), which are herein incorporated by reference.

Additional optional activators include metal salts of non-coordinating or weakly coordinating anions, for example where the metal is selected from Li, Na, K, Ag, Ti, Zn, Mg, Cs, and Ba.

It is within the scope of this invention that metal-ligand complexes and or ligand-metal-precursor-combinations can be combined with one or more activators or activation methods described above. For example, a combination of activators has been described in U.S. Pat. Nos. 5,153,157 and 5,453,410, EP0573120B1, and PCT publications WO94/07928 and WO95/14044. These documents all discuss the use of an alumoxane in combination with an ionizing activator.

Preferred activators used in the method of the present invention can be selected from the group consisting of modified methylalumoxane (MMAO), methylalumoxane (MAO), trimethylaluminum (TMA), triisobutyl aluminum (TIBA), polymethylalumoxane-IP (PMAO), N,N-di(n-decyl)-4-n-butyl-anilinium tetrakis(perfluorophenyl)borate, and mixtures thereof.

Typically, the molar ratio of metal (from the metal-ligand-complex or the ligand-metal-precursor-combination) to activator (specifically Cr: activator, specifically Cr: Al or Cr: B) can range from 1:1 to 1:5000. In another embodiment, the molar ratio of metal to activator employed can range from 1:1 to 1:500. In another embodiment, the molar ratio of metal to activator employed can range from 1:1 to 1:50. In another embodiment, the molar ratio of chromium to activator employed can range from 1:1 to 1:500. In another embodiment, the molar ratio of chromium to activator employed can range from 1:1 to 1:50.

In embodiments where more than one activator is used, the order in which the activators are combined with the metal-ligand-complex or the ligand-metal-precursor-combination may be varied.

Very generally, the oligomerization can be carried out in the Ziegler-Natta or Kaminsky-Sinn methodology, including temperatures from −100° C. to 300° C. and pressures from atmospheric to 3000 atmospheres (303,900 kPa). Suspension, solution, slurry, gas phase, or high-pressure oligomerization processes may be employed with the processes of this invention. Such processes can be run in a batch, semi-batch, or continuous mode.

Suitable solvents and or diluents for oligomerization are non-coordinating, inert liquids. Examples include mineral oil, straight and branched-chain hydrocarbons such as isobutane, butane, pentane, isopentane, hexane, isohexane, heptane, octane, dodecane, and mixtures thereof; cyclic and alicyclic hydrocarbons such as cyclohexane, cycloheptane, methylcyclohexane, methylcycloheptane, and mixtures thereof; perhalogenated hydrocarbons such as perfluorinated $C_{4-10}$ alkanes, chlorobenzene, and aromatic and alkylsubstituted aromatic compounds such as benzene, toluene, mesitylene, and xylene. Suitable solvents and or diluents also include liquid olefins which may act as monomers or comonomers including ethylene, propylene, 1-butene, 1-hexene, 1-pentene, 3-methyl-1-pentene, 4-methyl-1-pentene, 1-octene, and 1-decene. Mixtures of the foregoing are also suitable. With regard to catalyst solvent and or diluent and or diluent, there is flexibility as far as what catalyst solvent and or diluent and or diluent may be used. Particularly preferred solvents and or diluents include, but are not limited to, the comonomer product (e.g. 1-butene, 1-hexene, 1-octene), C4+ paraffins (e.g. isopentane, isobutane), cycloparaffins, and aromatics (e.g. toluene). If the catalyst is in the form of an immobilized or fixed bed, it may not require additional extraneous solvent and or diluent. In another exemplary embodiment, the catalyst to the comonomer synthesis reactor may be provided in the form of an immobilized or fixed bed, hence eliminating the need for a solvent and or diluent altogether.

Other additives that are useful in an oligomerization reaction may be employed, such as scavengers, promoters, modifiers, reducing agents, oxidizing agents, dihydrogen, aluminum alkyls, or silanes. For example, Jolly et al. (*Organometallics*, 16, pp 1511-1513 (1997)) has reported the use of magnesium as a reducing agent for Cr compounds that were synthesized as models for intermediates in selective ethylene oligomerization reactions.

In some useful embodiments, the activator (such as methylalumoxane or modified methylalumoxane-3A) is combined with the metal-ligand-complex or the ligand-metal-precursor-combination immediately prior to introduction into the reactor. Such mixing may be achieved by mixing in a separate tank then swift injection into the reactor, mixing in-line just prior to injection into the reactor, or the like. It has been observed that in some instances, a short activation time is very useful. Likewise in-situ activation, where the catalyst system components are injected separately into the reactor, with or without monomer, and allowed to combine within the reactor directly is also useful in the practice of this invention. In some embodiments, the catalyst system components are allowed to contact each other for 30 minutes or less, prior to contact with monomer, alternately for 5 minutes or less, alternately for 3 minutes or less, alternately for 1 minute or less.

The comonomer synthesis reactor may take various forms, including but not limited to, a stirred tank, a longer, thinner tube-like contactor or a bubble column. In an alternative embodiment, two or more comonomer synthesis reactors are configured in series. An advantage of series reactors is more thorough utilization of the catalyst, i.e. less nearly-fresh catalyst will get discharged with the product. Heat exchange capacity is also incorporated in the reactor or in a pumparound loop, to limit the exotherm. Where waxy buildup is an issue, spare heat exchangers may also be provided. Depending on the operating pressure of the reactor, the amount of the ethylene dissolved in the catalyst solvent and or diluent may also be controlled, which adds flexibility in the design of the reactor and the process as a whole.

Comonomer synthesis reaction conditions of the instant invention are selected and controlled to yield from about 40 to about 95% conversion of feed ethylene, and more preferably from about 60 to about 90% conversion of feed ethylene. For some of the chromium catalysts disclosed in U.S. Pat. No. 5,543,375, a range of reaction conditions are disclosed, which are herein incorporated by reference. One exemplary, but non-limiting set of reactor conditions is a temperature from about 80-150° C., and a pressure from about 300-900 psi. A preferred range of reactor temperature with an ethylene monomer is from about 60-110° C. Reaction conditions may be tuned to obtain desired phase separations as well as reactivity. In addition, reactor residence time is flexible, and may be chosen to provide a desired level of ethylene conversion. The residence time is a function of the type and amount of the catalyst utilized. In one exemplary embodiment when utilizing the chromium type catalysts disclosed in U.S. Pat. No. 5,543,375, the average residence time ranges from about 30 minutes to about 4 hours for a backmixed or pumparound reactor where most of the catalyst in the reactor at a given time is not "fresh," but has been circulating around for some time, and has become partially deactivated.

The effluent from the comonomer synthesis reactor is directed to a gas/liquid phase separator where most of the ethylene goes overhead for recycle to the reactor or to a separate process. A catalyst deactivator may be added to the effluent from the reactor to minimize further reactions in downstream equipment. Exemplary catalyst deactivators include, but are not limited to, water and alcohol. Exemplary gas/liquid phase separator types include, but are not limited to, a simple knockout vessel, flash drum or other single or multi-stage phase separators. The gas/liquid phase separator may also include some trays or packing in the zone where vapor is going up, with reflux. The ethylene stream exiting from the gas/liquid phase separator may be pressurized via a compressor or blower prior to being fed back to the comonomer synthesis reactor or to another separate process.

In an alternative embodiment, two or more gas/liquid phase separators are configured in series to further refine the separation of ethylene monomer for linear alpha olefin comonomer. In another alternative embodiment, some ethylene is added to the gas/liquid phase separator below the feed entrance point to strip out 1-hexene from the down-flowing solvent and or diluent. In another alternative embodiment, the ethylene recycle is dissolved in the recycled solvent and or diluent at low temperatures. This configuration allows for a simple pump to pressurize the feed mixture instead of a more expensive compressor or blower.

The liquid bottoms from the gas/liquid phase separator, containing catalyst, 1-hexene, other comonomers (octene, and decene), and catalyst solvent and or diluent, may then be conveyed to a distillation column. In a preferred embodiment, the catalyst is so selective that the amounts of C8-C10 byproducts produced are negligible, and so active that it can be diluted and disposed of in the hexene product. If these conditions are satisfied, the distillation column may function to separate the remaining ethylene from 1-hexene. The ethylene may then be recycled to the comonomer synthesis reactor, and the 1-hexene (containing spent catalyst) is discharged as product from the bottom of the column. In one exemplary embodiment where a very active and very selective catalyst is utilized to produce 1-hexene, a light catalyst solvent and or diluent may be used such that 1-hexene is collected as the bottom of the distillation column in very high purity, while the catalyst solvent and or diluent and the ethylene from the overhead are recycled back to the comonomer synthesis reactor.

In another exemplary embodiment where separation between 1-hexene and heavier products is required in addition to the ethylene/hexene separation, a single distillation column may be utilized by making it a divided-wall type column. In this configuration, the catalyst may be discharged with the heavy products. In another exemplary embodiment, a small post-column or other separation process is utilized to separate the catalyst from the heavy products, such that the catalyst may be mixed in with the 1-hexene for disposal. In addition, deactivation of the catalyst, may be utilized, for example, with the use of water.

In another alternative embodiment of the instant invention, the comonomer synthesis reactor and gas/liquid separator are combined into a single vessel for a classic catalytic distillation column, if compatible temperature and pressure can be found, and if sufficient residence time can be provided for reaction. This further simplifies the process complexity and the reduces costs associated with capital equipment and operating costs.

The linear alpha comonomer liquid product stream (1-butene, 1-hexene, 1-octene) resulting from the method of the instant invention is stored in tanks or other type of storage vessel prior to being transported to a subsequent process for further processing. The linear alpha olefin comonomers produced via the process of the instant invention may be used as the comonomer input of a polyolefin polymerization process, and a variety of other applications.

Applicants have attempted to disclose all embodiments and applications of the disclosed subject matter that could be reasonably foreseen. However, there may be unforeseeable, insubstantial modifications that remain as equivalents. While the present invention has been described in conjunction with specific, exemplary embodiments thereof, it is evident that many alterations, modifications, and variations will be apparent to those skilled in the art in light of the foregoing description without departing from the spirit or scope of the present disclosure. Accordingly, the present disclosure is intended to embrace all such alterations, modifications, and variations of the above detailed description The following simulated examples illustrate the present invention and the advantages thereto without limiting the scope thereof. The examples are based upon computer based simulations of the input streams and process conditions utilized for each of the exemplary process flow schematics illustrated.

EXAMPLES

For the purposes of the figures which follow in the simulated examples, "S" designates flow stream, "R" designates reactor, "F" designates gas/liquid phase separator, "C" designates compressor or blower, "M" designates mixing element, "P" designates pump, "SP" designates flow splitter, "E" designates heat exchanger, and "T" designates distillation column or tower. The number which follows each of the designations signifies the number of such element within the respective process schematic.

In examples 1-4, a 100% pure ethylene feed is utilized assuming 100% selectivity to produce an alpha-olefin product (either 1-butene or 1-hexene). These idealized conditions were selected for the purpose of determining equipment needs. In practice, the ethylene feed would be less than 100% pure (preferably 98.0-99.9% pure), and reaction selectivity would be less than 100% (e.g. 90-98%). In example 5, a polymer grade ethylene feed (99.9% ethylene and 0.1% ethane) is utilized with a reaction selectivity of 98% 1-hexene, 0.4% 1-octene and 1.6% C10 (1-decene and internal decenes).

Simulation Example 1

1-Hexene Product as a Catalyst Solvent

An exemplary process schematic using the 1-hexene product as the solvent is shown in FIG. 1. The ethylene feed is 100% ethylene while the reaction selectivity to 1-hexene is 100%. The feed is mixed with a recycled ethylene and 1-hexene stream S1 and is fed to reactor R2. The reactor R2 is operated at 90° C. and 400 psia and is sized to achieve 60% per pass conversion of ethylene. The product stream from the reactor S2 is separated from the unconverted ethylene using two flash drums F1, F2 operated at 400 and 14.96 psia respectively. The gas outlet S6 of the second flash drum F2 is then recompressed at 400 psia using a compressor C1 and recycled back to the reactor R2. The liquid stream S4 from the second flash drum F2, which includes >99.5% 1-hexene, is split into two streams, S10 and C6PRODUCT, using a flow splitter SP1. The S10 hexene stream is recycled acting as the catalyst solvent in comonomer synthesis process. Homogeneous or slurry catalyst leaves with the C6PRODUCT stream. A summary listing of stream flow rates and compositions is shown in Table 1. If conversion is increased to 90%, the ethylene concentration in the reactor product stream S2 is sufficiently low such that S2 becomes a single phase (liquid). In this case the first flash drum F1 can be eliminated, which further simplifies the process.

TABLE 1

Flow Rates and Compositions

| | Rate (lb/hr) | Ethylene | 1-Hexene |
|---|---|---|---|
| Ethylene Feed | 33700 | 100% | |
| Reactor Outlet | 89406 | 23.30% | 76.70% |
| 1-Hexene Product | 33696 | 0.80% | 99.20% |
| Recycle | 55706 | 18% | 82% |

Simulation Example 2

1-Hexene Product with Toluene as a Catalyst Solvent

Figure 2:
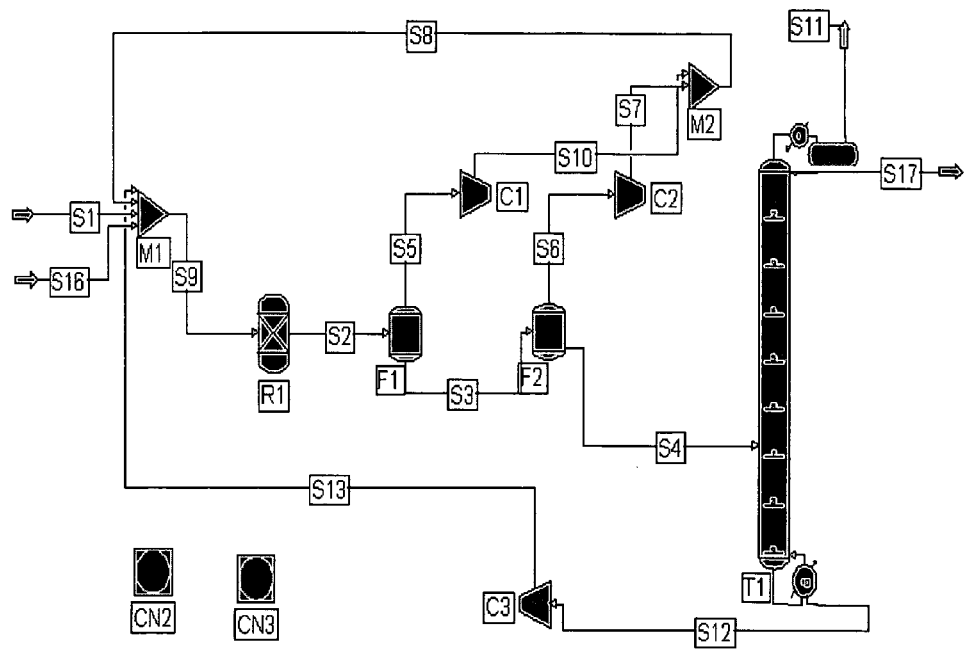
FIG. 2 depicts an exemplary process schematic of the process of the present invention for generating 1-hexene with toluene as a solvent and or diluent.

Another exemplary process using toluene as the catalyst solvent is shown in FIG. 2. The ethylene feed S1 is again 100% ethylene while the reaction selectivity to 1-hexene is 100%. The ethylene feed S1 is mixed through M1 with recycle stream S8 containing ethylene, solvent, and 1-hexene and is fed to reactor R1. The reactor R1 is operated at 100° C. and 400 psia and is sized to achieve 50% per pass conversion of ethylene. The product and the solvent are separated from the unconverted ethylene using two flash drums F1, F2 in series operated at 300 and 14.96 psia respectively. The gas outlets of the flash drums S5, S6 are recompressed to 400 psia, combined in one stream S8 and recycled back to the reactor R1. The liquid stream S4 from flash unit F2 is fed to a distillation column operation T1 at atmospheric pressure in order to separate 1-hexene S17 from the toluene solvent S12. The toluene solvent S12 collected at the bottom of the column is recycled via S13. Since the homogeneous or slurry catalyst leaves with the solvent, a portion of that recycled stream can be purged and fresh catalyst added to the system via S16 such that the activity of the catalyst in the reactor can be maintained constant. A summary listing of stream flow rates and compositions is shown in Table 2. An increase in the ethylene conversion would allow further simplification of the process similar to that of example 1.

TABLE 2

Flow Rates and Compositions

| | Rate (lb/hr) | Ethylene | Toluene | 1-Hexene |
|---|---|---|---|---|
| Ethylene Feed | 33700 | 100% | | |
| Solvent Feed | 100 | | 100.00% | |
| Recycle | 65800 | 76% | 4% | 20% |
| Solvent Recycle | 39700 | | 95% | 5% |
| Product | 31000 | 0.12% | 0.38% | 99.50% |

Simulation Example 3

1-Hexene Product with Isopentane as a Solvent—High Pressure

Figure 3:
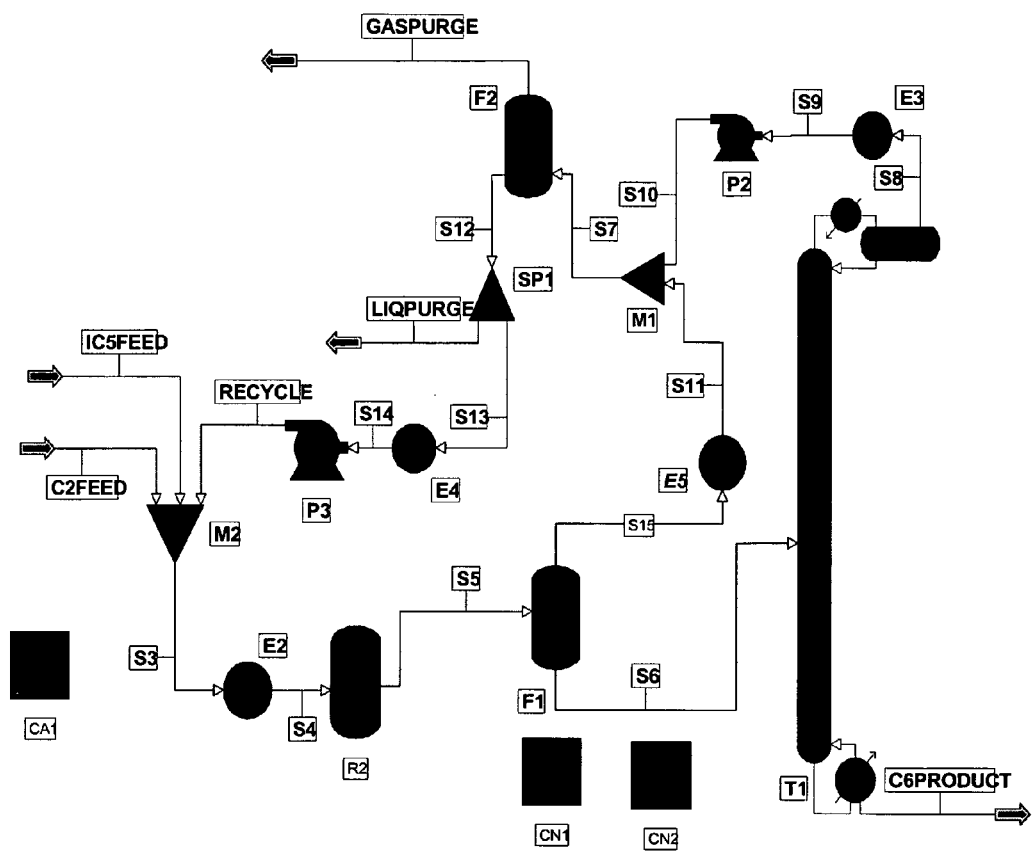
FIG. 3 depicts an exemplary process schematic of the process of the present invention for generating 1-hexene with isopentane as a solvent and or diluent at high pressure.

Another exemplary process using isopentane as the catalyst solvent at high pressure is shown in FIG. 3. Increasing the process pressure allows for an operation with the recycle stream as a liquid, which permits the use of a pump instead of an expensive compressor to transport the recycle stream. In this exemplary process, ethylene feed (C2FEED) is oligomerized to 1-hexene at 90° C. and 800 psia using isopentane, IC5FEED, as a catalyst solvent. The C2FEED is 100% ethylene while the reaction selectivity to 1-hexene is 100%. The feed is mixed with recycled ethylene, isopentane and 1-hexene (Recycle) and fed to the reactor R2. The reactor R2 is operated at 90° C. and 800 psia and is sized to achieve 80% per pass conversion of ethylene. The reactor product stream S5 is then fed to a flash drum F1 where the 1-hexene stream S6 is separated from the unconverted ethylene and catalyst solvent stream S15 at 150 psia. The bottoms stream S6 from the flash drum F1 is then fed to a distillation column T1 operated at 60 psia to complete the separation of 1-hexene, C6PRODUCT, from unconverted ethylene and catalyst solvent S8. The C6PRODUCT, including the homogeneous/slurry catalyst, is collected at the bottom of the distillation column. The overhead vapors of unconverted ethylene and catalyst solvent S8 from the distillation column T1 are condensed to form a liquid stream S9 using a heat exchanger E3 and transported using a pump P2 operated at 150 psia. The condensed unconverted ethylene and catalyst solvent stream S10 and a condensed overhead vapor stream S11 from the from the flash drum F1 are mixed through a mixing element M1. The combined stream S7 is separated into a gas and liquid phase in second flash drum F2. The liquid stream S13 is then subcooled through a heat exchanger E4, pumped back to 800 psia using a pump P3 and recycled back to the reactor R2 as a recycle stream (RECYCLE). A summary listing of stream flow rates and compositions is shown in Table 3.

TABLE 3

Flow Rates and Compositions

|  | Rate (lb/hr) | Ethylene | Isopentane | 1-Hexene |
|---|---|---|---|---|
| Ethylene Feed | 33700 | 100% |  |  |
| Solvent Feed | 142 |  | 100.00% |  |
| Recycle | 50428 | 34% | 63% | 3% |
| Product | 33700 | 0.00% | 0.50% | 99.50% |

Simulated Example 4

1-Butene Product with Isopentane as a Solvent—High Pressure

Figure 4:
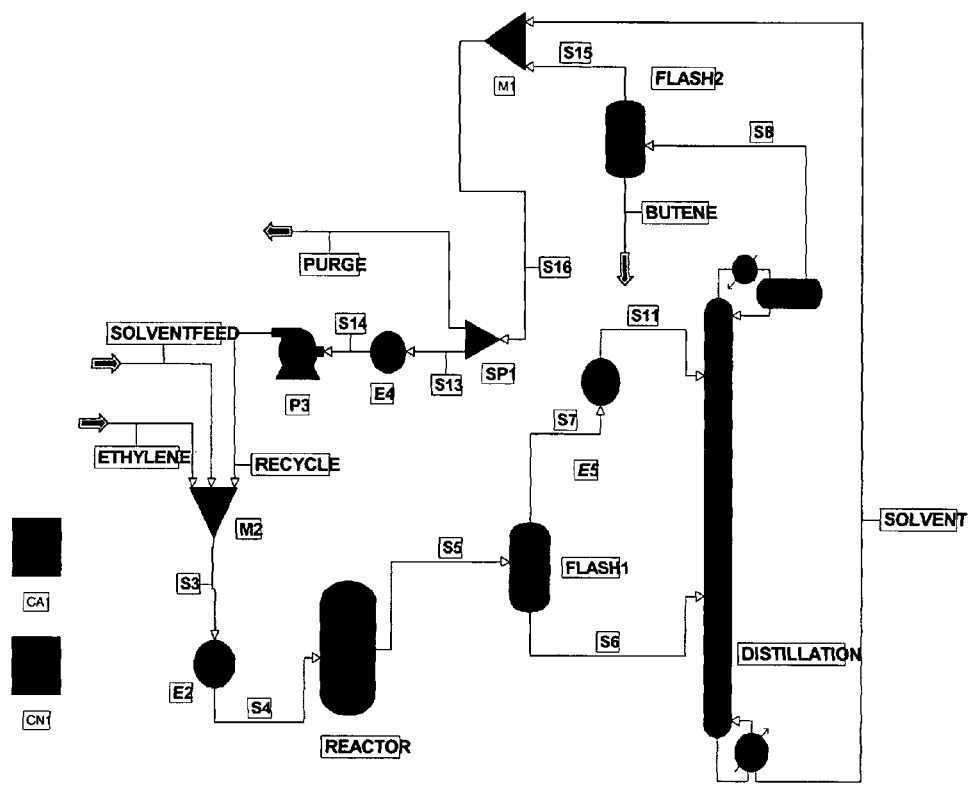
FIG. 4 depicts an exemplary process schematic of the process of the present invention for generating 1-butene with isopentane as a solvent and or diluent at high pressure.

Another exemplary process to produce 1-butene using isopentane as the catalyst solvent at high pressure is shown in FIG. 4. In this example, the conditions and the process flow schematic are similar to Example 3. However, instead of a 1-hexene selective catalyst, a 1-butene selective catalyst is used. 1-butene is lighter than isopentane and is collected as the overhead vapor S8 from the distillation column operating at 60 psia. The vapors, which are a mixture of 1-butene and ethylene are then cooled to −20° C., and the liquid product is separated in a second flash drum, FLASH2, operating at 50 psia. The product stream, BUTENE, from the second flash drum, FLASH2, is 85.5% 1-butene. This product stream, BUTENE, can be directly fed to a polyethylene reactor (not shown). However if a higher purity is needed a second distillation column instead of the second flash drum, FLASH2, may be used. The overhead vapors from the second flash drum, FLASH2, are mixed through a mixing device M1 with the recycled isopentane stream from the distillation column, SOLVENT, condensed through a heat exchanger, E4, and pumped with a pump P3 to 800 psia, and then recycled as a recycle stream (RECYCLE) to the reactor. A summary listing of stream flow rates and compositions is shown in Table 4.

TABLE 4

Flow Rates and Compositions

|  | Rate (lb/hr) | Ethylene | Isopentane | 1-Butene |
|---|---|---|---|---|
| Ethylene Feed | 33700 | 100% |  |  |
| Solvent Feed | 308 |  | 100.00% |  |
| Recycle | 47072 | 24.20% | 70.90% | 4.90% |
| Product | 34008 | 14.50% | 0.00% | 85.50% |

Simulated Example 5

1-Hexene Product with Isopentane Solvent w/Polymer Grade Feed

Figure 5:
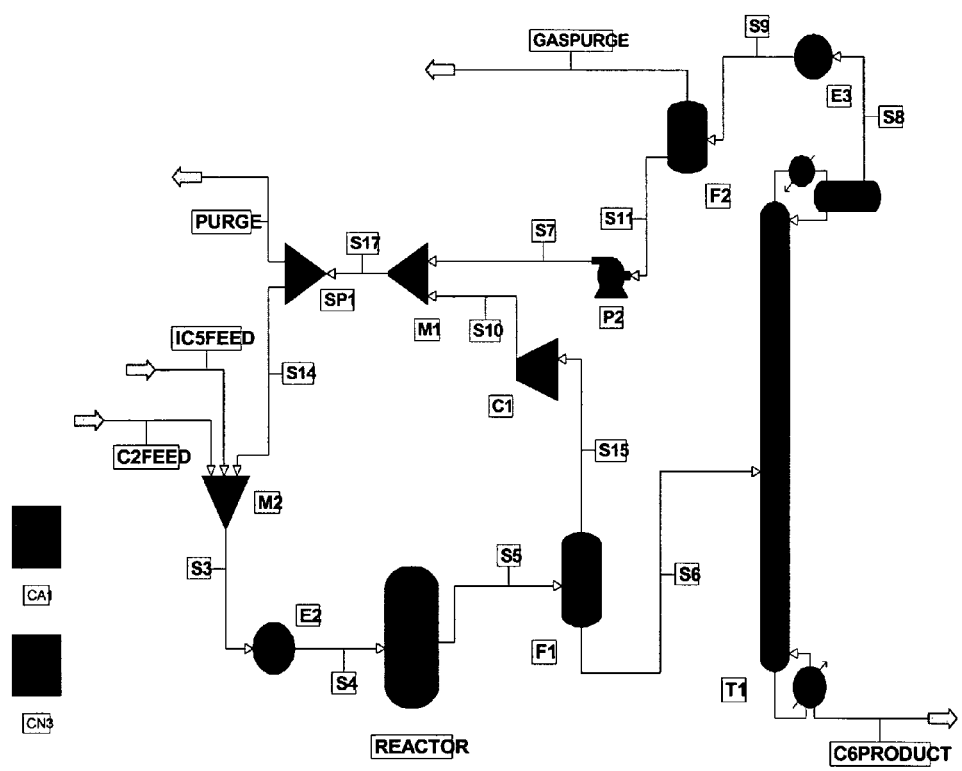
FIG. 5 depicts an exemplary process schematic of the process of the present invention for generating 1-hexene with isopentane as a solvent and or diluent and using polymer grade feed.
Figure 6:
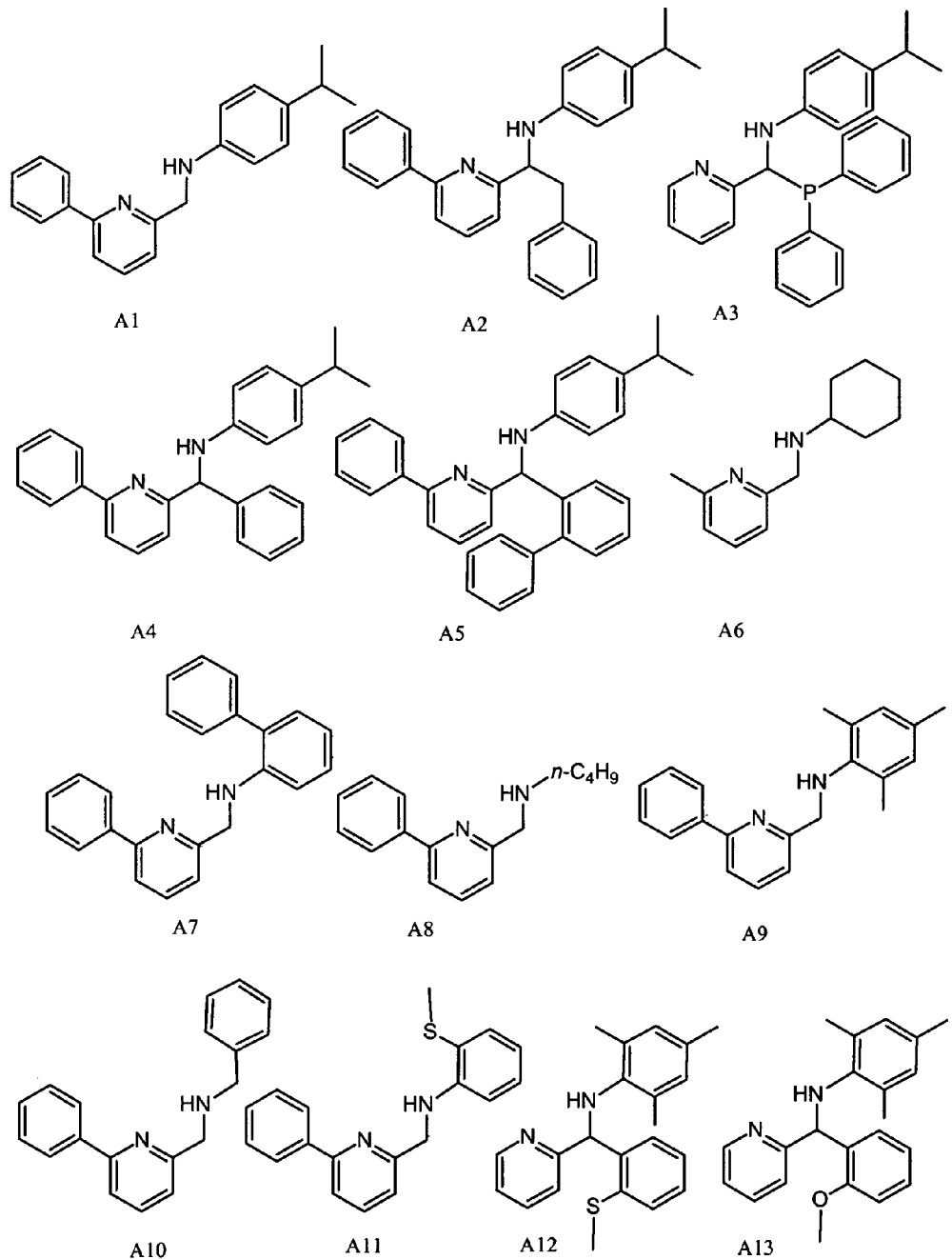
FIG. 6 illustrates pyridyl-amine ligands A1-A13.
Figure 7:
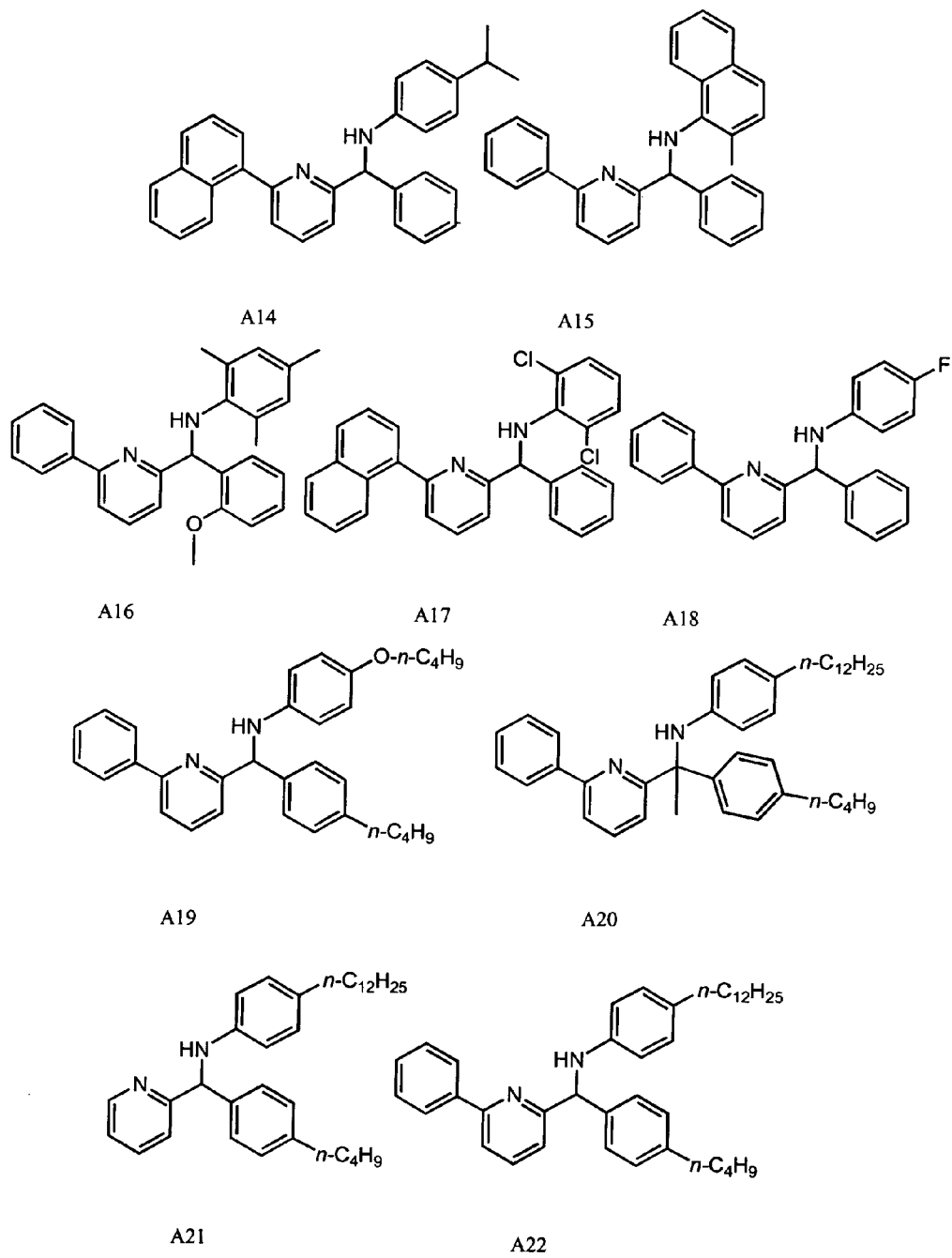
FIG. 7 illustrates pyridyl-amine ligands A14-A22.
Figure 8:
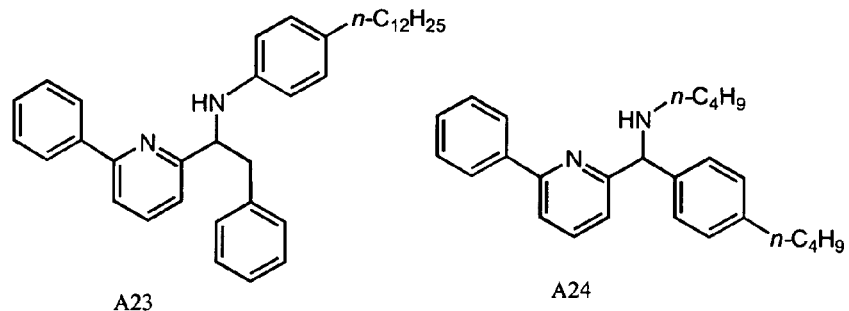
FIG. 8 illustrates pyridyl-amine ligands A23-A32.
Figure 8:
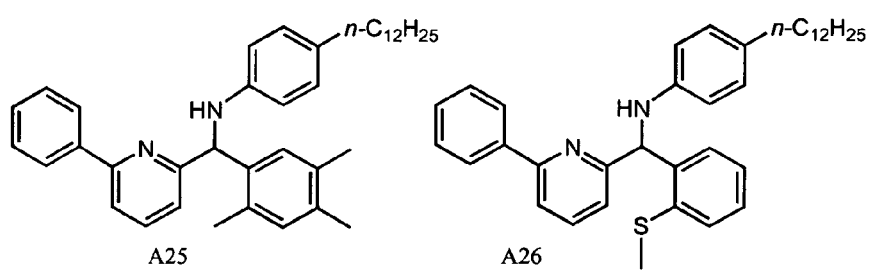
Figure 8:
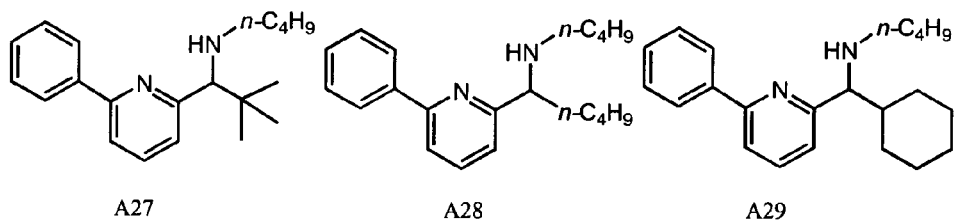
Figure 8:
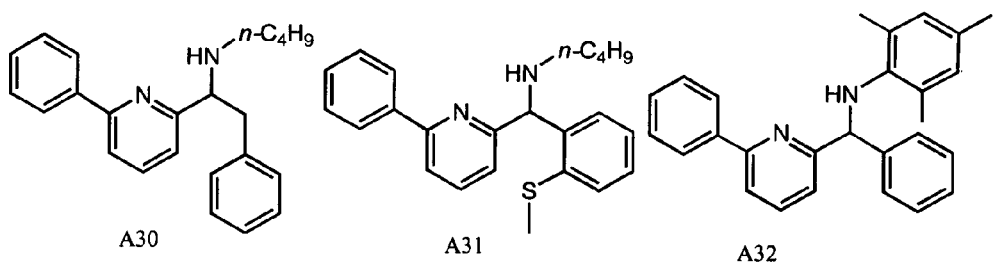
Figure 9:
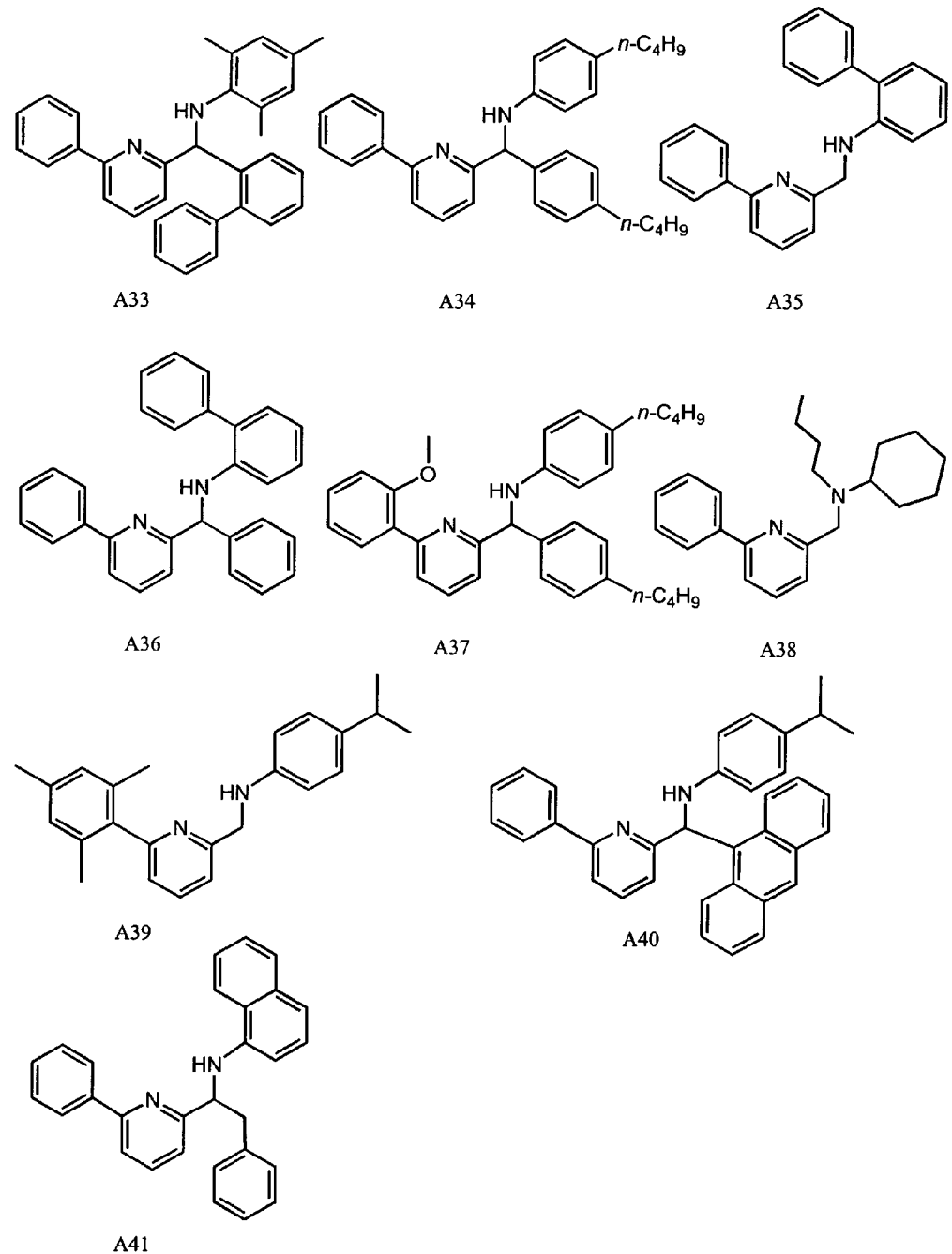
FIG. 9 illustrates pyridyl-amine ligands A33-A41.
Figure 10:
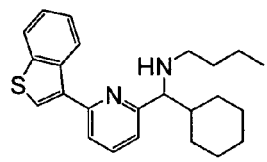
FIG. 10 illustrates pyridyl-amine ligands A42-A52.
Figure 10:
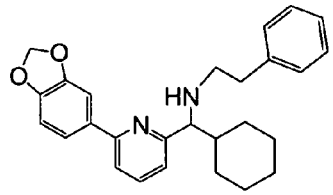
Figure 10:
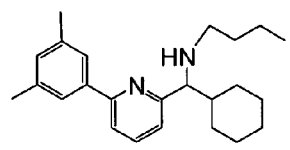
Figure 10:
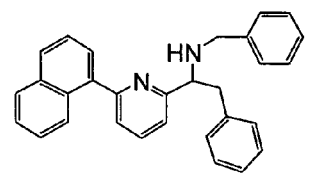
Figure 10:
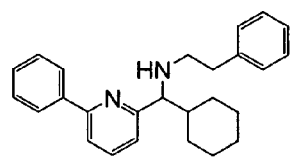
Figure 10:
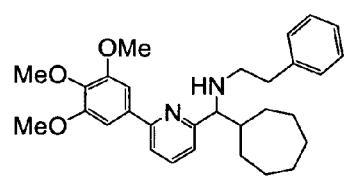
Figure 10:
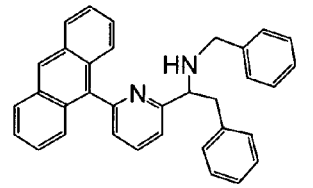
Figure 10:
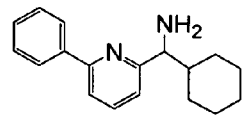
Figure 10:
Figure 10:
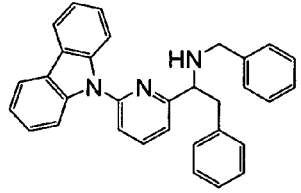
Figure 10:
Figure 10:
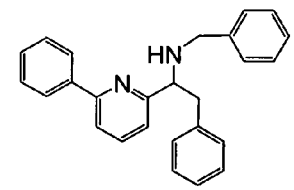
Figure 10:
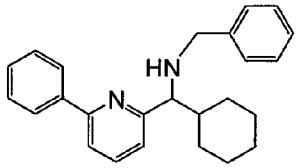
Figure 11:
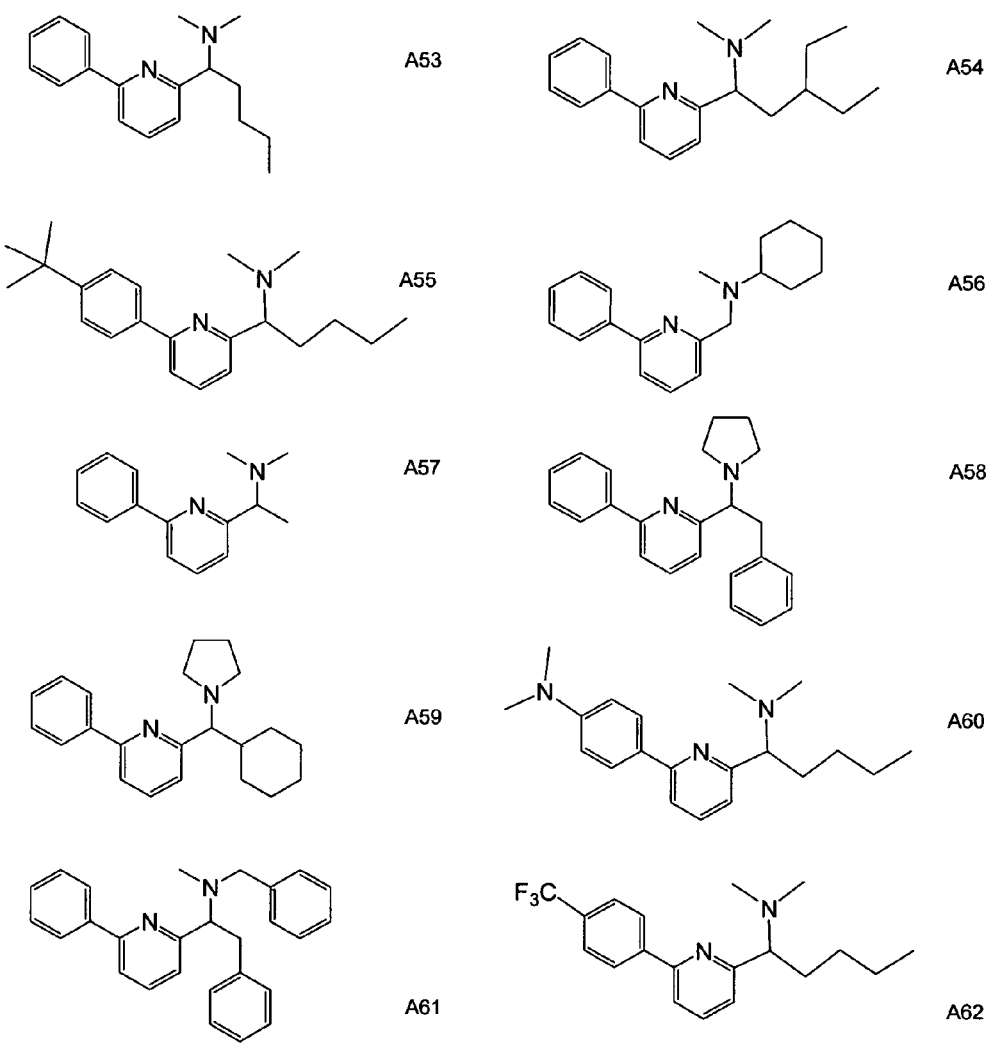
FIG. 11 illustrates pyridyl-amine ligands A53-A62
Figure 12:
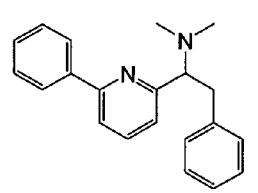
FIG. 12 illustrates pyridyl-amine ligands A63-A75.
Figure 12:
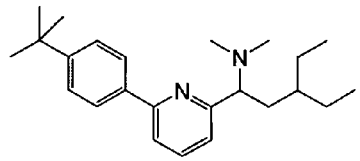
Figure 12:
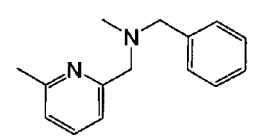
Figure 12:
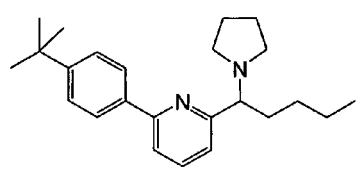
Figure 12:
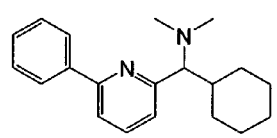
Figure 12:
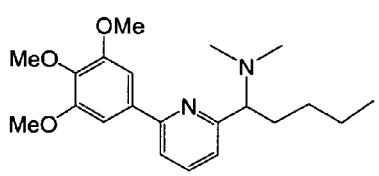
Figure 12:
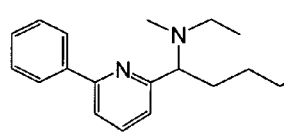
Figure 12:
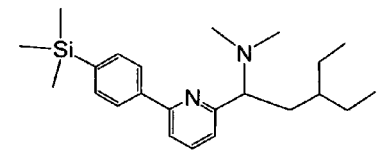
Figure 12:
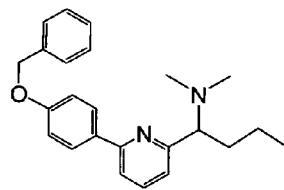
Figure 12:
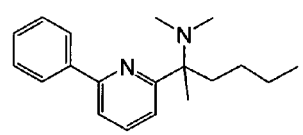
Figure 12:
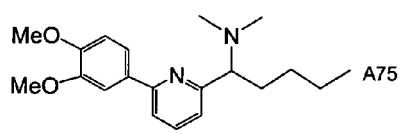

Another exemplary process to produce 1-hexene using isopentane as the catalyst solvent with a polymer grade ethylene feed is shown in FIG. 5. The ethylene feed, C2 FEED, is 99.9% ethylene and 0.1% ethane (polymer grade feed) while the reaction selectivity to 1-hexene is 98% 1-hexene, 0.4% 1-octene and 1.6% decenes (both 1-decene and internals). The feed is mixed through a mixing device M2 with recycled ethylene S14 and isopentane IC5FEED and fed to the reactor. The reactor is operated at 90° C. and 400 psia and is sized to achieve 80% per pass conversion of ethylene. The product stream from the reactor S5 is separated from unconverted ethylene using a flash drum F1 operated at 200 psia. The gas outlet S15 of the flash drum F1 is then recompressed through a compressor C1 at 400 psia and recycled. The liquid stream S6 from the flash drum F1 is fed to a distillation column T1 operating at 60 psia. At the bottom of the distillation column 1-hexene and the heavier alpha-olefins are collected as the product stream from the column C6PRODUCT. The overhead vapors from the column S8 are then cooled at 0° C. using a heat exchanger E3 and conveyed to a second flash drum F2. The liquid phase S1 from the second flash drum F2 containing mostly ethylene is pumped using a pump P2 to 400 psia and recycled back to the reactor. The gas phase, GASPURGE, is purged from the second flash drum F2. Homogeneous or slurry catalyst leaves with the 1-hexene product, C6PPRODUCT. A summary listing of stream flow rates and compositions is shown in Table 5.

TABLE 5

Flow Rates and Compositions

|  | Rate (lb/hr) | Ethylene | Isopentane | 1-hexene | 1-octene | Decenes | Ethane |
|---|---|---|---|---|---|---|---|
| Ethylene Feed | 33700 | 99.9% |  |  |  |  | 0.1% |
| Solvent Feed | 2230 |  | 100.00% |  |  |  |  |
| Recycle | 28169 | 41.14% | 53.57% | 4.55% |  |  | 0.74% |
| Product | 31632 | 0.00% | 0.29% | 98.41% | 0.30% | 1.00% |  |

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law.

What is claimed is:

1. A method for preparing linear alpha olefin comonomers from ethylene monomer comprising the following steps:
providing one or more comonomer synthesis reactors configured in series, and one or more downstream gas/liquid phase separators, which are not distillation columns, configured in series;
feeding an ethylene monomer, and a catalyst in a solvent and/or diluent to said one or more comonomer synthesis reactors;
reacting in said one or more comonomer synthesis reactors said ethylene monomer and said catalyst in solvent and/or diluent under reaction conditions to produce an effluent stream comprising unreacted ethylene monomer, said catalyst in a solvent and/or diluent, and comonomer;
passing said effluent stream to said one or more downstream gas/liquid phase separators to form a gas stream of said unreacted ethylene monomer, and a liquid stream of said comonomer and said catalyst in a solvent and/or diluent, without distillation;
recycling to said one or more comonomer synthesis reactors said unreacted ethylene monomer and a portion of said liquid stream; and
storing a remaining portion of said liquid stream for subsequent processing of said comonomer;
wherein said comonomer is selected from the group consisting of 1-butene, 1-hexene, 1-octene, 1-decene and mixtures thereof, and is similar in composition to said solvent and or diluent, wherein the catalyst comprises the combination of:

1) a ligand represented by the formula:

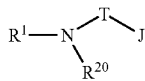

wherein:
N is nitrogen;
$R^1$ and $R^{20}$ are each independently selected from the group consisting of consisting of hydrogen and optionally substituted hydrocarbyl, heteroatom containing hydrocarbyl and silyl, provided that $R^1$ or $R^{20}$ do not equal T-J, alternately $R^1$ and $R^{20}$ are each independently a ring having from 4 to 8 atoms in the ring selected from the group consisting of substituted cycloalkyl, heterocycloalkyl, aryl and heteroaryl);
T is a bridging group, preferably represented by the formula -(T'$R^2R^3$)—, where T' is carbon or silicon, $R^2$ and $R^3$ are each independently selected from the group consisting of hydrogen, halogen, and optionally substituted alkyl, heteroalkyl, aryl, heteroaryl, alkoxy, aryloxy, silyl, boryl, phosphino, amino, alkylthio, arylthio, and combinations thereof, provided that two or more $R^2$ and/or $R^3$ groups may be joined together to form one or more optionally substituted ring systems having from 3 to 50 non-hydrogen atoms;
J is an optionally substituted six-membered heterocycle, containing at least one nitrogen atom as part of the ring, or J is an optionally substituted five-membered heterocycle, containing at least one nitrogen atom as part of the ring;
or a ligand represented by the formula:

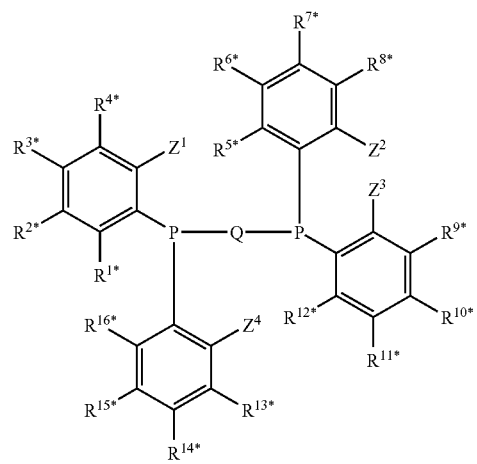

wherein
P is phosphorus;
each of $R^{1*}$, $R^{2*}$, $R^{3*}$, $R^{4*}$, $R^{5*}$, $R^{6*}$, $R^{7*}$, $R^{8*}$, $R^{9*}$, $R^{10*}$, $R^{11*}$, $R^{12*}$, $R^{13*}$, $R^{14*}$, $R^{15*}$, and $R^{16*}$ is, independently, selected from the group consisting of hydrogen, halogen, optionally substituted hydrocarbyl and optionally substituted heteroatom containing hydrocarbyl;
each of $Z^1$, $Z^2$, $Z^3$ or $Z^4$ is, independently, selected from the group consisting of hydrogen, a hydrocarbyl, alkoxy, aryloxy, alkylthio, arylthio, hydroxyl, mercapto and amino;
Q is a bridging group selected from the group consisting of optionally substituted hydrocarbyl having from 2 to 20 carbon atoms;

2) a metal precursor compound characterized by the general formula Cr(L)$_n$ where each L is independently selected from the group consisting of halide, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, ether, thioether, carboxylates, thio, 1,3-dionates, oxalates, carbonates, nitrates, sulfates, ethers, thioethers and combinations thereof, wherein two or more L groups may be combined in a ring structure having from 3 to 50 non-hydrogen atoms; and n is 1, 2, 3, 4, 5, or 6; and 3) optionally, one or more activators.

2. The method of claim 1, wherein said comonomer is used in a polyethylene polymerization reactor.

3. The method of claim 1, wherein said one or more comonomer synthesis reactors are a stirred tank reactor, a long, thin tube-like contactor, or a bubble column type reactor.

4. The method of claim 1, wherein said ethylene monomer is greater than 99% about ethylene.

5. The method of claim 1, wherein the ligand of the catalyst is represented by the formula:

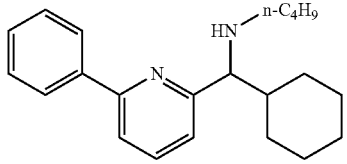

A29 or

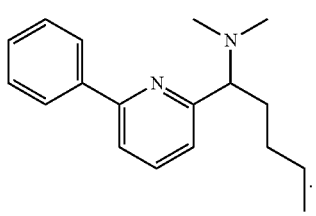

A53

6. The method of claim 1, wherein said catalyst comprises one or more activators.

7. The method of claim 1, wherein said solvent and/or diluent is selected from the group consisting of 1-butene, 1-hexene, 1-octene, toluene, isobutane, and isopentane.

8. The method of claim 7, wherein said solvent and/or diluent is 1-hexene.

9. The method of claim 1, wherein said reaction conditions yield from about 40% to about 95% conversion of said ethylene monomer.

10. The method of claim 9, wherein said reaction conditions yield from about 60% to about 90% conversion of said ethylene monomer.

11. The method of claim 9, wherein said reaction conditions comprise a reaction temperature from about 80 to about 150° C., a reaction pressure from about 300 to about 900 psi, and a reaction residence time from about 30 minutes to about 4 hours.

12. The method of claim 1, wherein a catalyst deactivator is added to said effluent stream exiting from said one or more comonomer synthesis reactors, wherein said catalyst deactivator is water or alcohol.

13. The method of claim 1, wherein said one or more downstream gas/liquid phase separators comprise a knockout vessel, a flash drum, or a stirred tank or pot.

14. The method of claim 13, wherein said one or more downstream gas/liquid phase separators further comprise trays or packing in the vapor zone.

15. The method of claim 1 further comprising the step of adding ethylene monomer to said one or more downstream gas/liquid phase separators to strip out comonomer from said liquid stream.

16. A method for preparing linear alpha olefin comonomers from ethylene monomer comprising the following steps:

providing one or more comonomer synthesis reactors configured in series, one or more downstream gas/liquid phase separators, which are not distillation columns, configured in series, and one or more distillation columns configured in series;

feeding an ethylene monomer, and a catalyst in a solvent and or and/or diluent to said one or more comonomer synthesis reactors;

reacting in said one or more comonomer synthesis reactors said ethylene monomer and said catalyst in solvent and/or diluent under reaction conditions to produce an effluent stream comprising unreacted ethylene monomer, said catalyst in a solvent and/or diluent, and comonomer;

passing said effluent stream to said one or more downstream gas/liquid phase separators to form a gas stream of said unreacted ethylene monomer, and a liquid stream of said comonomer and said catalyst in a solvent and/or diluent, without distillation;

passing said liquid stream of said comonomer and said catalyst in a solvent and/or diluent to said one or more distillation columns to separate said comonomer from said catalyst in a solvent and/or diluent;

recycling to said one or more comonomer synthesis reactors said unreacted ethylene monomer and said catalyst in a solvent and/or diluent; and storing said comonomer for subsequent processing;

wherein said comonomer is selected from the group consisting of 1-butene, 1-hexene, 1-octene, 1-decene and mixtures thereof, wherein the catalyst comprises the combination of:

1) a ligand represented by the formula:

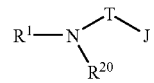

wherein:

N is nitrogen;

$R^1$ and $R^{20}$ are each independently selected from the group consisting of consisting of hydrogen and optionally substituted hydrocarbyl, heteroatom containing hydrocarbyl and silyl, provided that $R^1$ or $R^{20}$ do not equal T-J, alternately $R^1$ and $R^{20}$ are each independently a ring having from 4 to 8 atoms in the ring selected from the group consisting of substituted cycloalkyl, heterocycloalkyl, aryl and heteroaryl);

T is a bridging group, preferably represented by the formula -(T'$R^2R^3$)—, where T' is carbon or silicon, $R^2$ and $R^3$ are each independently selected from the group consisting of hydrogen, halogen, and optionally substituted alkyl, heteroalkyl, aryl, heteroaryl, alkoxy, aryloxy, silyl, boryl, phosphino, amino, alkylthio, arylthio, and combinations thereof, provided that two or more $R^2$ and/or $R^3$ groups may be joined together to form one or more optionally substituted ring systems having from 3 to 50 non-hydrogen atoms;

J is an optionally substituted six-membered heterocycle, containing at least one nitrogen atom as part of the ring, or J is an optionally substituted five-membered heterocycle, containing at least one nitrogen atom as part of the ring;

or a ligand represented by the formula:

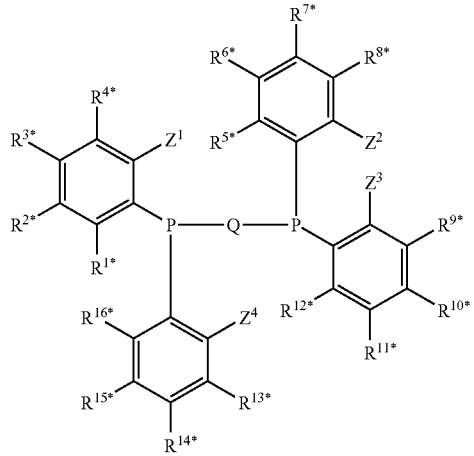

wherein
  P is phosphorus;
  each of $R^{1*}, R^{2*}, R^{3*}, R^{4*}, R^{5*}, R^{6*}, R^{7*}, R^{8*}, R^{9*}, R^{10*}, R^{11*}, R^{12*}, R^{13*}, R^{14*}, R^{15*}$, and $R^{16*}$ is, independently, selected from the group consisting of hydrogen, halogen, optionally substituted hydrocarbyl and optionally substituted heteroatom containing hydrocarbyl;
  each of $Z^1, Z^2, Z^3$ or $Z^4$ is, independently, selected from the group consisting of hydrogen, a hydrocarbyl, alkoxy, aryloxy, alkylthio, arylthio, hydroxyl, mercapto and amino;
  Q is a bridging group selected from the group consisting of optionally substituted hydrocarbyl having from 2 to 20 carbon atoms;

2) a metal precursor compound characterized by the general formula $Cr(L)_n$ where each L is independently selected from the group consisting of halide, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, ether, thioether, carboxylates, thio, 1,3-dionates, oxalates, carbonates, nitrates, sulfates, ethers, thioethers and combinations thereof, wherein two or more L groups may be combined in a ring structure having from 3 to 50 non-hydrogen atoms; and n is 1, 2, 3, 4, 5, or 6; and 3) optionally, one or more activators.

17. The method of claim 16, wherein said comonomer is used in a polyethylene polymerization reactor.

18. The method of claim 16, wherein said one or more comonomer synthesis reactors are a stirred tank reactor, a long, thin tube-like contactor, or a bubble column type reactor.

19. The method of claim 16, wherein said ethylene monomer feed is greater than about 99% ethylene.

20. The method of claim 16, wherein the ligand of said catalyst is represented by the formula:

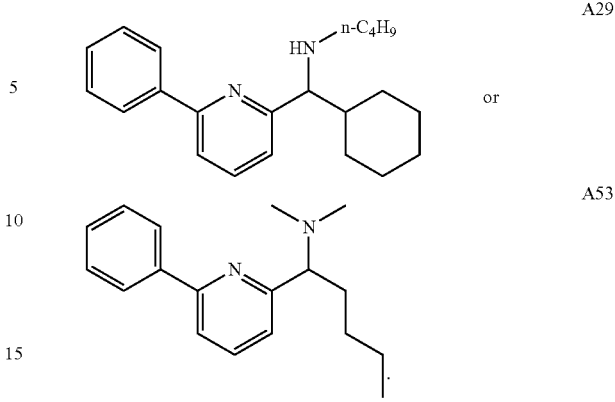

21. The method of claim 16, wherein said catalyst further comprises one or more activators.

22. The method of claim 16, wherein said solvent and/or diluent is selected from the group consisting of 1-butene, 1-hexene, 1-octene, toluene, isobutane, and isopentane.

23. The method of claim 16, wherein said reaction conditions yield from about 40% to about 95% conversion of said ethylene monomer.

24. The method of claim 23, wherein said reaction conditions yield from about 60% to about 90% conversion of said ethylene monomer.

25. The method of claim 23, wherein said reaction conditions comprise a reaction temperature from about 80 to about 150° C., a reaction pressure from about 300 to about 900 psi, and a reaction residence time from about 30 minutes to about 4 hours.

26. The method of claim 16, wherein a catalyst deactivator is added to said effluent stream exiting from said one or more comonomer synthesis reactors, wherein said catalyst deactivator is water or alcohol.

27. The method of claim 16, wherein said one or more downstream gas/liquid phase separators comprises a knockout vessel, a flash drum, or a stirred tank or pot.

28. The method of claim 27, wherein said one or more downstream gas/liquid phase separators further comprises trays or packing in the vapor zone.

29. The method of claim 16 further comprising the step of adding ethylene monomer to said one or more downstream gas/liquid phase separators to strip out comonomer from said liquid stream.

30. The method of claim 16 wherein said one or more distillation columns separate said catalyst in solvent and/or diluent from the top and said comonomer from the bottom.

31. The method of claim 30 wherein said one or more distillation columns further separate residual ethylene monomer from the top.

32. The method of claim 30 wherein said one or more distillation column is a divided wall type column.

33. The method of claim 16 wherein said one or more distillation column separate said comonomer from the top and said catalyst in solvent and/or diluent from the bottom.

34. A method for preparing linear alpha olefin comonomers from ethylene monomer comprising the following steps:

providing a combination comonomer synthesis reactor and gas/liquid phase separator, which is not a distillation column, into a single vessel;

feeding an ethylene monomer, and a catalyst in a solvent and/or diluent to said combination comonomer synthesis reactor and gas/liquid phase separator;

reacting in said combination comonomer synthesis reactor and gas/liquid phase separator said ethylene monomer and said catalyst in solvent and/or diluent under reaction conditions to produce an effluent stream from said gas/liquid separator comprising a gas stream of unreacted ethylene monomer and a liquid stream of comonomer and catalyst in a solvent and/or diluent;

recycling to said combination comonomer synthesis reactor and gas/liquid phase separator said gas stream and a portion of said liquid stream; and storing a remaining portion of said liquid stream for subsequent processing of said comonomer;

wherein said comonomer is selected from the group consisting of 1-butene, 1-hexene, 1-octene, 1-decene and mixtures thereof, wherein the catalyst comprises the combination of:

1) a ligand represented by the formula:

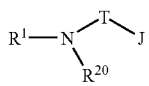

wherein:

N is nitrogen;

$R^1$ and $R^{20}$ are each independently selected from the group consisting of consisting of hydrogen and optionally substituted hydrocarbyl, heteroatom containing hydrocarbyl and silyl, provided that $R^1$ or $R^{20}$ do not equal T-J, alternately $R^1$ and $R^{20}$ are each independently a ring having from 4 to 8 atoms in the ring selected from the group consisting of substituted cycloalkyl, heterocycloalkyl, aryl and heteroaryl);

T is a bridging group, preferably represented by the formula -(T'$R^2R^3$)—, where T' is carbon or silicon, $R^2$ and $R^3$ are each independently selected from the group consisting of hydrogen, halogen, and optionally substituted alkyl, heteroalkyl, aryl, heteroaryl, alkoxy, aryloxy, silyl, boryl, phosphino, amino, alkylthio, arylthio, and combinations thereof, provided that two or more $R^2$ and/or $R^3$ groups may be joined together to form one or more optionally substituted ring systems having from 3 to 50 non-hydrogen atoms;

J is an optionally substituted six-membered heterocycle, containing at least one nitrogen atom as part of the ring, or J is an optionally substituted five-membered heterocycle, containing at least one nitrogen atom as part of the ring;

or a ligand represented by the formula:

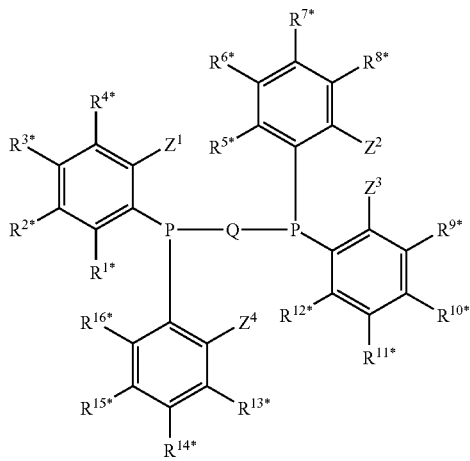

wherein
P is phosphorus;
each of $R^{1*}$, $R^{2*}$, $R^{3*}$, $R^{4*}$, $R^{5*}$, $R^{6*}$, $R^{7*}$, $R^{8*}$, $R^{9*}$, $R^{10*}$, $R^{11*}$, $R^{12*}$, $R^{13*}$, $R^{14*}$, $R^{15*}$, and $R^{16*}$ is, independently, selected from the group consisting of hydrogen, halogen, optionally substituted hydrocarbyl and optionally substituted heteroatom containing hydrocarbyl;
each of $Z^1$, $Z^2$, $Z^3$ or $Z^4$ is, independently, selected from the group consisting of hydrogen, a hydrocarbyl, alkoxy, aryloxy, alkylthio, arylthio, hydroxyl, mercapto and amino;
Q is a bridging group selected from the group consisting of optionally substituted hydrocarbyl having from 2 to 20 carbon atoms;

2) a metal precursor compound characterized by the general formula Cr(L)$_n$ where each L is independently selected from the group consisting of halide, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, ether, thioether, carboxylates, thio, 1,3-dionates, oxalates, carbonates, nitrates, sulfates, ethers, thioethers and combinations thereof, wherein two or more L groups may be combined in a ring structure having from 3 to 50 non-hydrogen atoms; and n is 1, 2, 3, 4, 5, or 6; and 3) optionally, one or more activators.

35. The method of claim 34, wherein said comonomer is used in a polyethylene polymerization reactor.

36. The method of claim 34, wherein said ethylene monomer feed is greater than about 99% ethylene.

37. The method of claim 34, wherein the ligand of said catalyst is represented by the formula:

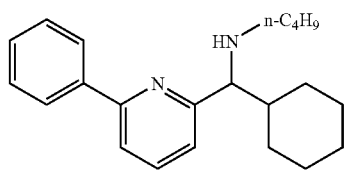

A29 or

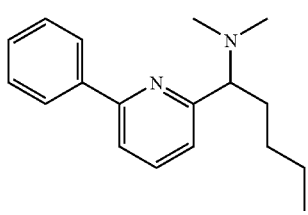
A53

38. The method of claim 34, wherein said catalyst comprises one or more activators.

39. The method of claim 34, wherein said solvent and/or diluent is selected from the group consisting of 1-butene, 1-hexene, 1-octene, toluene, isobutane, and isopentane.

40. The method of claim 34, wherein said reaction conditions yield from about 40% to about 95% conversion of said ethylene monomer.

41. The method of claim 1 wherein the ligand of the catalyst is represented by the formula:

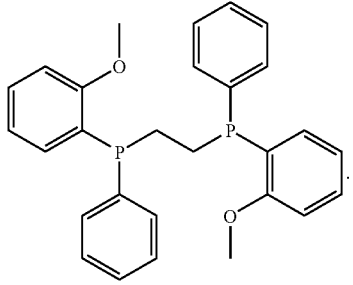
A2

42. The method of claim 16 wherein the ligand of the catalyst is represented by the formula:

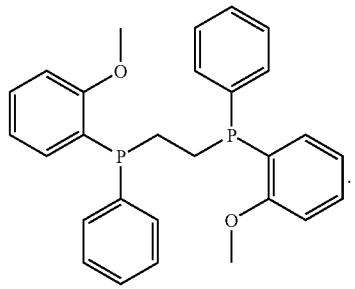
A2

43. The method of claim 34 wherein the ligand of the catalyst is represented by the formula:

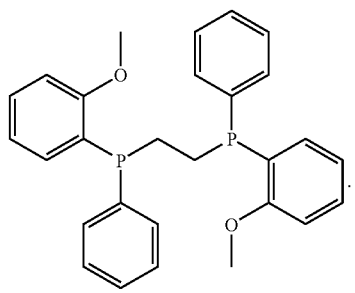
A2

* * * * *